United States Patent
Paul et al.

(10) Patent No.: US 10,420,804 B2
(45) Date of Patent: Sep. 24, 2019

(54) THERAPEUTIC COMPOSITIONS AND USES THEREOF

(71) Applicant: Manuka Health New Zealand Limited, Auckland (NZ)

(72) Inventors: Kerry Paul, Auckland (NZ); Owen John Catchpole, Auckland (NZ); Darina Lazarova, Scranton, PA (US)

(73) Assignee: Manuka Health New Zeland Limited, Auckland (NZ)

( * ) Notice: Subject to any disclaimer, the term of this patent is extended or adjusted under 35 U.S.C. 154(b) by 0 days.

(21) Appl. No.: 15/465,414

(22) Filed: Mar. 21, 2017

(65) Prior Publication Data

US 2017/0290865 A1 Oct. 12, 2017

Related U.S. Application Data

(63) Continuation of application No. 14/781,863, filed as application No. PCT/NZ2014/000060 on Apr. 7, 2014, now abandoned.

(30) Foreign Application Priority Data

Apr. 5, 2013 (NZ) ........................................ 609074

(51) Int. Cl.
| | | |
|---|---|---|
| *A61K 35/644* | (2015.01) | |
| *A61K 47/69* | (2017.01) | |
| *A61K 9/16* | (2006.01) | |
| *A61K 47/40* | (2006.01) | |
| *A61K 35/63* | (2015.01) | |
| *A61K 9/19* | (2006.01) | |
| *A61K 45/06* | (2006.01) | |
| *A61K 31/192* | (2006.01) | |
| *A61K 31/216* | (2006.01) | |
| *A61K 31/352* | (2006.01) | |
| *A61K 31/353* | (2006.01) | |
| *A61K 9/51* | (2006.01) | |

(52) U.S. Cl.
CPC .......... *A61K 35/644* (2013.01); *A61K 9/1652* (2013.01); *A61K 9/19* (2013.01); *A61K 9/5161* (2013.01); *A61K 31/192* (2013.01); *A61K 31/216* (2013.01); *A61K 31/352* (2013.01); *A61K 31/353* (2013.01); *A61K 35/63* (2015.01); *A61K 45/06* (2013.01); *A61K 47/40* (2013.01); *A61K 47/6951* (2017.08)

(58) Field of Classification Search
None
See application file for complete search history.

(56) References Cited

U.S. PATENT DOCUMENTS

| | | |
|---|---|---|
| 5,561,116 A | 10/1996 | Nakamura et al. |
| 5,922,324 A | 7/1999 | Aga et al. |
| 2016/0030364 A1 | 2/2016 | Paul et al. |
| 2016/0051594 A1* | 2/2016 | Paul ...................... A61K 35/63 424/493 |

FOREIGN PATENT DOCUMENTS

| | | |
|---|---|---|
| CN | 1451390 | 10/2003 |
| EP | 0867187 | 9/1998 |
| EP | 2671596 | 12/2013 |
| WO | WO 2012/073051 | 6/2012 |

OTHER PUBLICATIONS

Hernandez et al., Sonoran Propolis: Chemical . . . Planta Med 2007; 73: 1469-1474 (Year: 2007).*
Ribeiro et al., Caffeic Acid Phenethyl Ester (CAPE) May be a Promising Adjuvant Treatment in Gastric Cancer, J Clin Gastroenterol vol. 41, No. 10, Nov./Dec. 2007 (Year: 2007).*
Written Opinion of the International Searching Authority for corresponding international application No. PCT/NZ2014/000060, dated Jul. 10, 2014.
Coneac et al. (2008) "Propolis extract/β-cyclodextrin nanoparticles: synthesis, physico-chemical, and multivariate analyses", Journal of Agroalimentary Processes and Technologies 14:58-70.
Kalogeropoulos et al. (2009) "Encapsulation of complex extracts in β-cyclodextrin: An application to propolis ethanolic extract",Journal of Microencapsulation 26(7): 603-613.
Nafady et al. (2003) "Cyclodextrin-Enclosed Substances of Brazilian Propolis", Chem. Pharm. Bull. 51(8): 984-985.
Sawicka et al (2012) "The anticancer activity of propolis", Folia Histochemica et Cytobiologica 50(1): 25-37.
European Extended Search Report, dated Dec. 1, 2016, corresponding to European Application No. 14779790.6 (filed Feb. 17, 2016), a related application, 12 pp.
USIA et al. (2002) "Constituents of Chinese Propolis and Their Antiproliferative Activities," J. Nat. Prod. 65:673-676.
Li et al. (2010) "Cytotoxicity of Constituents from Mexican Propolis Against a Panel of Six Different Cancer Cell Lines," Natural Product Communications 5(10):1601-1606.
Mutalifu et al. (2012) "The Effects of Propolis Lfavonoid Pinobanksin-3-acetate on Cell Proliferation, Apoptosis and Gene Expression of Human Colorectal Cancer Cell Lines," Xinjiang University, Biochemistry and Molecular Biology, Master's thesis, Abstract only.
Ribeiro et al., Caffeic Acid Phenethyl Ester (CAPE) May be a Promising Adjuvant Treatment in Gastric Cancer, J Clin Gastroenterol vol. 41, No. 10, Nov./Dec. 2007.
Japanese Office Action, dated Dec. 14, 2017, in Japanese Patent Application No. 2016- 506282, a related application, 4 pp. (English translation).

(Continued)

*Primary Examiner* — Jennifer A Berrios
(74) *Attorney, Agent, or Firm* — Leydig, Voit & Mayer, Ltd.

(57) ABSTRACT

This invention provides pharmaceutical compositions, including anti-gastrointestinal cancer compositions, containing propolis and cyclodextrin. Methods of using such compositions, in particular in the treatment or prevention of gastrointestinal cancers, and the resensitization of gastrointestinal cancers to therapy are also provided.

16 Claims, 2 Drawing Sheets

(56) References Cited

OTHER PUBLICATIONS

Bankova et al. (2002) "Chemical Composition of European Propolis: Expected and Unexpected Resu," Z. Naturforsch, 57c: 530-533.

Banskota et al. (2000) "Cytotoxic, Hepatoprotective and Free Radical Scavenging Effects of Propolis from Brazil, Peru, the Netherlands and China," J. Ethnopharmacol., 72:239-246.

Banskota et al. (2002) "Antiproliferative Activity of the Netherlands Propolis and its Active Principles in Cancer Cell Lines," J. Ethnopharmacol., 80:67-73.

Mateescu, C. (1999) "Propolis as a Therapeutic Agent," Mitsubachi Kagaku Honeybee Science 20(2):51-61.

Cho et al., 2016, *"Effects of propolis and gamma-cyclodextrin on intestinal neoplasia in normal weight and obese mice"*, Cancer Med., 5(9): 2448-2458.

Chinese First Office Action, dated Jun. 27, 2018, in Chinese Patent Application No. 201480030083.7, a related application, 15 pp.

\* cited by examiner

THERAPEUTIC COMPOSITIONS AND USES THEREOF

CROSS-REFERENCE TO RELATED APPLICATIONS

This application is a continuation of U.S. application Ser. No. 14/781,863, filed Oct. 1, 2015, which is a U.S. National Stage application filed under 35 U.S.C. § 371 of International Application No. PCT/NZ2014/000060, filed Apr. 7, 2014, which claims the benefit of New Zealand Application No. 609074, filed Apr. 5, 2013. All of these applications are hereby incorporated by reference in their entireties.

FIELD OF INVENTION

This invention relates to compositions for the treatment and prevention of gastrointestinal cancers. In particular, this invention relates to anti-gastrointestinal cancer compositions containing propolis and cyclodextrin, including anti-gastrointestinal cancer compositions comprising one or more propolis extracts. Particularly contemplated are anti-gastrointestinal cancer compositions comprising propolis and γ-cyclodextrin, for example European propolis and γ-cyclodextrin, and the use of such compositions in the treatment or prevention of gastrointestinal cancers such as colorectal, gastric and throat cancers.

BACKGROUND OF THE INVENTION

Crude propolis is a resinous substance produced by bees from the resin collected from botanical sources, such as buds and sap, which is admixed with beeswax. The colour of crude propolis can vary from yellow, through browns to almost black depending on the botanical source. Beeswax is normally separated from the propolis by extraction using ethanol, in which the wax is insoluble but the resinous compounds are highly soluble. There are a number of types of propolis, which are based on the botanical sources of resin compounds, and the geographical region. The most well-known types of propolis are "European" propolis, where the resin compounds are obtained by bees mostly from leaf and bud exudates of poplars, and to a lesser extent birches and willows; and "Brazilian Green" propolis, which is mainly obtained by bees from leaf exudates of the tree *Baccharis dracanculifolia*. Propolis produced in New Zealand can be categorized as "European" as its composition broadly matches other European propolis (Markham et al, 1996. HPLC and GC-MS identification of the major organic constituents in New Zealand propolis. *Phytochemistry*, 42(1): 205-211). Crude propolis and extracts derived from propolis have been reported to have antibacterial, antifungal, and antiviral activities. Its use in the treatment of several types of cancer, in particular breast cancer, has also been investigated.

Identification and verification of the anti-cancer constituent(s) present in propolis resin has been challenging because of the complex and multicomponent nature of the resin. In Brazilian Green propolis, the anti-cancer activity is mainly attributed to artepillan C, while in European propolis resin the anti-cancer activity is mainly attributed to caffeic acid phenethyl ester (CAPE), a dihydroxy cinnamic acid ester; and chrysin, an aglycone flavonoid, see for example, Sawicka et al (2012) "The anticancer activity of propolis", *Folia Histochemica et Cytobiologica*, 50 (1), 25-37.

Colorectal cancer is reportedly the second and third most common cancer in women and men, respectively, from developed countries. Colorectal cancer is more prevalent in developed countries—the US, Australia, Europe, and New Zealand having the highest rates—with incidence being as much as 10 times greater than in developing countries. While surgery can be effective, early detection is critical to positive surgical outcomes. Other therapies are largely directed at life extension and palliative care, as the efficacy of current chemotherapies and radiotherapies in treating primary tumours, or metastases outside the lymph nodes is debated.

Throat cancer, also referred to as oesophaegeal cancer, pharyngeal cancer, or laryngeal cancer, encompasses tumours that develop in the tissues of the pharynx, nasopharynx, oropharynx, hypopharynx, larynx (voice box) or tonsils. Therapies for throat cancer include surgery, radiotherapy or chemotherapy. Treatment for throat cancer can damage the throat and may cause changes to the way a patient eats, breathes and sleeps.

Gastric or stomach cancer is the second most common cause of cancer-related death in the world. Diagnosis is often delayed because symptoms may not occur in the early stages of the disease. Surgery to remove the stomach (gastrectomy) is the only treatment that can cure gastric cancers. Chemotherapy and radiation therapy after surgery may improve the chance of a cure.

Accordingly, there is a need for anti-gastrointestinal cancer compositions, including those suitable for use in the treatment or prevention of colorectal cancer, gastric cancer and throat cancer and those which are able to support the maintenance of anti-gastrointestinal cancer activity or augment anti-gastrointestinal cancer activity.

It is an object of the present invention to provide anti-gastrointestinal cancer compositions, including stable anti-gastrointestinal cancer compositions for use in the treatment or prevention of colorectal cancer, gastric cancer and throat cancer, or to at least provide the public with a useful choice.

SUMMARY OF THE INVENTION

Accordingly, in a first aspect the invention relates to an anti-gastrointestinal cancer composition comprising propolis and cyclodextrin, and in particular, gamma cyclodextrin.

In one embodiment the anti-gastrointestinal composition is an anti-colorectal cancer composition. In another embodiment the anti-gastrointestinal composition is an anti-gastric cancer composition. In a further embodiment the anti-gastrointestinal composition is an anti-throat cancer composition.

In another aspect, the present invention relates to a pharmaceutical composition comprising, consisting essentially of, or consisting of propolis and gamma-cyclodextrin. In one embodiment, the composition is for maintaining or improving gut health. Accordingly, in one embodiment the invention relates to a pharmaceutical composition for maintaining or improving gut health, the composition comprising, consisting essentially of, or consisting of propolis and cyclodextrin.

In one embodiment the propolis is propolis resin. In one embodiment the resin is propolis resin and the cyclodextrin is gamma-cyclodextrin.

In another aspect the invention relates to a method of treating or preventing a gastrointestinal cancer in a subject, the method comprising administering an effective amount of a composition comprising, consisting essentially of, or consisting of propolis and cyclodextrin, to a subject in need thereof.

In another aspect the invention relates to a method of inhibiting gastrointestinal tumour formation, inhibiting gastrointestinal tumour growth, inhibiting gastrointestinal tumour metastasis or treating or preventing a gastrointestinal cancer in a subject, the method comprising separate, simultaneous or sequential administration of an effective amount of a composition comprising, consisting essentially of, or consisting of propolis and cyclodextrin, to a subject in need thereof.

Another aspect of the invention relates to a method of inducing apoptosis of one or more neoplastic gastrointestinal cells in a subject, the method comprising administration of an effective amount of a composition comprising, consisting essentially of, or consisting of propolis and cyclodextrin, to a subject in need thereof.

In one embodiment the apoptosis is of gastrointestinal tumour cells, such as colorectal, gastric or throat tumour cells.

Another aspect of the invention relates to a method of modulating proliferation of one or more neoplastic gastrointestinal cells in a subject, the method comprising administration of an effective amount of a composition comprising, consisting essentially of, or consisting of propolis and cyclodextrin, to a subject in need thereof.

For example in one embodiment the modulation is reduction. Accordingly the invention relates to a method of reducing proliferation of one or more neoplastic gastrointestinal cells in a subject, the method comprising administration of an effective amount of a composition comprising, consisting essentially of, or consisting of propolis and cyclodextrin, to a subject in need thereof.

In one embodiment the proliferation is of gastrointestinal tumour cells, such as colorectal, gastric or throat tumour cells.

Another aspect of the invention relates to a method of increasing the responsiveness of a subject to a gastrointestinal cancer therapy comprising administration to the subject of a composition comprising, consisting essentially of, or consisting of propolis and cyclodextrin.

Another aspect of the invention relates to a method of increasing the sensitivity of a gastrointestinal tumour in a subject to a gastrointestinal cancer therapy comprising administration to the subject of a composition comprising, consisting essentially of, or consisting of propolis and cyclodextrin.

In a further aspect, the invention relates to a method of resensitising one or more gastrointestinal cancer cells that are resistant to treatment, the method comprising administering an effective amount of a composition comprising, consisting essentially of, or consisting of propolis and cyclodextrin to the one or more gastrointestinal cancer cells.

In one embodiment, the gastrointestinal cancer cells comprise a tumour present in a subject. In one embodiment the gastrointestinal cancer cells are colorectal cancer cells. In another embodiment the gastrointestinal cancer cells are gastric cancer cells. In a further embodiment the gastrointestinal cancer cells are throat cancer cells.

The invention also relates to a method of at least partially reversing the resistance of a neoplastic cell in a subject suffering from a gastrointestinal cancer to a gastrointestinal cancer therapy, the method comprising administration to the subject of a composition comprising, consisting essentially or, or consisting of propolis and cyclodextrin.

The present invention further relates to a method of reversing, wholly or in part, the resistance of a gastrointestinal cancer-burdened patient to a gastrointestinal cancer therapy, the method comprising the step of administering to said patient a composition comprising, consisting essentially of, or consisting of propolis and cyclodextrin.

In another aspect, the invention provides a method of re-sensitising one or more tumours of a gastrointestinal cancer-burdened patient which are, or are predicted to either be or become, resistant to treatment with a gastrointestinal cancer therapy, said method comprising the step of administering to said patient a composition comprising, consisting essentially or, or consisting of propolis and cyclodextrin.

In one embodiment, the one or more tumours are or are predicted to be or to become resistant to a gastrointestinal cancer therapy due increased activation of one or more pro-cancer cell survival signaling pathways within the one or more tumours or within the patient, including increased activation of one or more of the AKT, JNK or JAK/STAT signaling pathways, for example within a sample from the patient, such as a tissue sample, a tumour biopsy, or a blood or plasma sample.

In one embodiment, the invention provides a method of inactivating or suppressing one or more pro-cancer cell survival signalling pathways within the one or more tumours or within the patient. For example, the invention relates to a method of inactivating or suppressing one or more of the AKT, JNK or JAK/STAT signaling pathways within the one or more tumours.

In one embodiment, the one or more tumours are or are predicted to be or to become resistant to a gastrointestinal cancer therapy due to increased activation of one or more of the AKT, JNK or JAK/STAT signaling pathways within the tumour(s).

In one embodiment, the invention provides a method of preventing tumours becoming resistant to a primary gastrointestinal cancer therapy, wherein the resistance is at least in part mediated by increased activation of one or more of the AKT, JNK or JAK/STAT signaling pathways, for example within the tumour(s).

In one embodiment, the tumours are resistant to treatment with a chemotherapeutic.

In one embodiment the gastrointestinal cancer is colorectal cancer. In another embodiment the gastrointestinal cancer is gastric cancer. In a further embodiment the gastrointestinal cancer is throat cancer.

In still a further aspect, the present invention relates to a method of improving gut health, the method comprising administering to a subject in need thereof a composition comprising, consisting essentially of, or consisting of propolis and cyclodextrin; and in particular, propolis and gamma-cyclodextrin, for example European propolis and gamma-cyclodextrin.

In a further aspect, the invention provides a synergistic composition comprising propolis and gamma-cyclodextrin. In one embodiment, the composition is a synergistic therapeutic composition. In one embodiment, the composition provides a synergistic therapeutic effect.

In one embodiment the propolis and gamma-cyclodextrin provide a synergistic therapeutic effect that is greater than the effect of either one alone or greater than the additive effects of either one alone. For example, there is a greater effect on induction of apoptosis, on gastrointestinal cancer cell survival or proliferation, on resensitisation to therapy, on treatment or prevention of gastrointestinal cancer, or the responsiveness of a subject or a tumour to the treatment method. In one embodiment, the propolis and gamma-cyclodextrin allow the administration of a co-administered or sequentially administered gastrointestinal cancer therapy to be reduced or increased in dose or in length of administration, as appropriate.

Another aspect of the invention relates to use of propolis and cyclodextrin in the manufacture of a composition for a purpose as herein described.

Another aspect of the invention relates to use of propolis and gamma-cyclodextrin with at least one additional therapeutic agent in the manufacture of a composition for a purpose as herein described.

Another aspect of the invention relates to use of a complex comprising propolis and gamma-cyclodextrin, with at least one additional therapeutic agent in the manufacture of a composition for a purpose as herein described, wherein the composition is formulated to provide separate, simultaneous or sequential administration of the propolis and gamma-cyclodextrin complex and the at least one additional therapeutic agent.

Another aspect of the invention relates to a composition comprising, consisting essentially of or consisting of propolis and gamma-cyclodextrin.

Another aspect of the invention relates to a product comprising, consisting essentially of or consisting of propolis and gamma-cyclodextrin, optionally with one or more, two or more or three or more additional therapeutic agents as a combined preparation for simultaneous, separate or sequential use for a purpose as described herein.

Another aspect of the invention relates to a composition of the invention for use in the treatment or prevention of a gastrointestinal cancer.

The following embodiments may relate to any of the above aspects.

In various embodiments, the cyclodextrin is gamma-cyclodextrin, or the cyclodextrin is present as a combination of cyclodextrins comprising gamma-cyclodextrin.

In one embodiment, the cyclodextrin is chemically-modified cyclodextrin.

In one embodiment, the propolis is present in the anti-gastrointestinal cancer composition as a propolis extract or fraction.

In one embodiment, the propolis present in the anti-gastrointestinal cancer composition is free of wax. For example, the propolis has been dewaxed using extraction processes known in the art.

In one embodiment, the propolis is "European" or "Poplar" propolis. For example, the "European" propolis is at least in part derived from the bud and leaf exudates of one or more species of poplars, birches, larches or willows. In another embodiment, the propolis is "Brazilian Green" propolis. For example, the "Brazilian" propolis is at least in part obtained by bees from leaf exudates of the tree *Baccharis dracanculifolia*.

In one embodiment, the composition comprises from about 1.0% wt to about 99% wt propolis. In an alternative embodiment the composition comprises from about 1.0% wt to about 99% wt propolis resin.

In various embodiments, the composition comprises from about 1% wt to about 99% wt propolis, from about 1% wt to about 25% wt propolis, from about 1% wt to about 30% wt propolis, from about 5% wt to about 25% wt propolis, from about 5% wt to about 30% wt propolis, from about 5% wt to about 99% wt propolis, from about 10% wt to about 25% wt propolis, from about 10% wt to about 30% wt propolis, from about 10% wt to about 99% wt propolis, from about 15% wt to about 25% wt, from about 15% wt to about 30% wt, from about 15% wt to about 99% wt, from about 20% wt to about 25% wt, from about 20% wt to about 30% wt, from about 20% wt to about 99% wt, or about 25% wt propolis, or about 30% wt propolis.

In various embodiments, the composition comprises from about 1% wt to about 99% wt propolis resin, from about 1% wt to about 25% wt propolis resin, from about 1% wt to about 30% wt propolis resin, from about 5% wt to about 25% wt propolis resin, from about 5% wt to about 30% wt propolis resin, from about 5% wt to about 99% wt propolis resin, from about 10% wt to about 25% wt propolis resin, from about 10% wt to about 30% wt propolis resin, from about 10% wt to about 99% wt propolis resin, from about 15% wt to about 25% wt, from about 15% wt to about 30% wt, from about 15% wt to about 99% wt, from about 20% wt to about 25% wt, from about 20% wt to about 30% wt, from about 20% wt to about 99% wt, or about 25% wt propolis resin, or about 30% wt propolis resin.

In one embodiment the propolis in the composition is entirely encapsulated within the cyclodextrin.

In one embodiment the molar ratio of propolis to cyclodextrin in the composition is no greater than about 1:1.

In one embodiment, the European propolis comprises caffeic acid phenylether ester (CAPE). In one embodiment the European propolis comprises chrysin. In one embodiment the European propolis comprises caffeic acid. In one embodiment the European propolis comprises benzyl caffeate. In one embodiment the European propolis comprises pinobanksin. In one embodiment the European propolis comprises pinocembrin. In one embodiment the European propolis comprises galangin.

In various embodiments, the European propolis comprises any combination of two or more of CAPE, chrysin, galangin, pinocembrin, pinobanksin, benzyl caffeate, and caffeic acid.

In one embodiment, the European propolis has a CAPE concentration of greater than about 1 mg/g, than about 1.5 mg/g, than about 2 mg/g, about 2.5 mg/g, about 3 mg/g, about 3.5 mg/g, about 4 mg/g, about 4.5 mg/g, about 5 mg/g, about 5.5 mg/g, about 6 mg/g, about 7.5 mg/g, about 10 mg/g, about 15 mg/g, about 20 mg/g, about 25 mg/g, about 30 mg/g, about 40 mg/g, about 50 mg/g, about 75 mg/g, about 100 mg/g, about 125 mg/g, about 150 mg/g, about 175 mg/g, about 200 mg/g, 250 mg/g, about 300 mg/g, about 350 mg/g, about 400 mg/g, about 450 mg/g, about 500 g/g, about 550 mg/g, about 600 mg/g, about 650 mg/g, about 700 mg/g, about 750 mg/g, about 800 mg/g, about 850 mg/g, about 900 mg/g, about 950 mg/g, up to about 1000 mg/g.

In one embodiment, the European propolis has a pinocembrin concentration of greater than about 1 mg/g, than about 1.5 mg/g, than about 2 mg/g, about 2.5 mg/g, about 3 mg/g, about 3.5 mg/g, about 4 mg/g, about 4.5 mg/g, about 5 mg/g, about 5.5 mg/g, about 6 mg/g, about 7.5 mg/g, about 10 mg/g, about 15 mg/g, about 20 mg/g, about 25 mg/g, about 30 mg/g, about 40 mg/g, about 50 mg/g, about 75 mg/g, about 100 mg/g, about 125 mg/g, about 150 mg/g, about 175 mg/g, about 200 mg/g, 250 mg/g, about 300 mg/g, about 350 mg/g, about 400 mg/g, about 450 mg/g, about 500 mg/g, about 550 mg/g, about 600 mg/g, about 650 mg/g, about 700 mg/g, about 750 mg/g, about 800 mg/g, about 850 mg/g, about 900 mg/g, about 950 mg/g, up to about 1000 mg/g.

In one embodiment, the European propolis has a galangin concentration of greater than about 1 mg/g, than about 1.5 mg/g, than about 2 mg/g, about 2.5 mg/g, about 3 mg/g, about 3.5 mg/g, about 4 mg/g, about 4.5 mg/g, about 5 mg/g, about 5.5 mg/g, about 6 mg/g, about 7.5 mg/g, about 10 mg/g, about 15 mg/g, about 20 mg/g, about 25 mg/g, about 30 mg/g, about 40 mg/g, about 50 mg/g, about 75 mg/g, about 100 mg/g, about 125 mg/g, about 150 mg/g, about 175 mg/g, about 200 mg/g, 250 mg/g, about 300 mg/g, about 350 mg/g, about 400 mg/g, about 450 mg/g, about 500 mg/g, about 550 mg/g, about 600 mg/g, about 650 mg/g, about 700 mg/g, about 750 mg/g, about 800 mg/g, about 850 mg/g, about 900 mg/g, about 950 mg/g, up to about 1000 mg/g.

In one embodiment, the European propolis has chrysin concentration of greater than about 1 mg/g, than about 1.5 mg/g, than about 2 mg/g, about 2.5 mg/g, about 3 mg/g, about 3.5 mg/g, about 4 mg/g, about 4.5 mg/g, about 5 mg/g, about 5.5 mg/g, about 6 mg/g, about 7.5 mg/g, about 10 mg/g, about 15 mg/g, about 20 mg/g, about 25 mg/g, about 30 mg/g, about 40 mg/g, about 50 mg/g, about 75 mg/g, about 100 mg/g, about 125 mg/g, about 150 mg/g, about 175 mg/g, about 200 mg/g, 250 mg/g, about 300 mg/g, about 350 mg/g, about 400 mg/g, about 450 mg/g, about 500 mg/g, about 550 mg/g, about 600 mg/g, about 650 mg/g, about 700 mg/g, about 750 mg/g, about 800 mg/g, about 850 mg/g, about 900 mg/g, about 950 mg/g, up to about 1000 mg/g.

In one embodiment, the European propolis has benzyl caffeate concentration of greater than about 1 mg/g, than about 1.5 mg/g, than about 2 mg/g, about 2.5 mg/g, about 3 mg/g, about 3.5 mg/g, about 4 mg/g, about 4.5 mg/g, about 5 mg/g, about 5.5 mg/g, about 6 mg/g, about 7.5 mg/g, about 10 mg/g, about 15 mg/g, about 20 mg/g, about 25 mg/g, about 30 mg/g, about 40 mg/g, about 50 mg/g, about 75 mg/g, about 100 mg/g, about 125 mg/g, about 150 mg/g, about 175 mg/g, about 200 mg/g, about 250 mg/g, about 300 mg/g, about 350 mg/g, about 400 mg/g, about 450 mg/g, about 500 mg/g, about 550 mg/g, about 600 mg/g, about 650 mg/g, about 700 mg/g, about 750 mg/g, about 800 mg/g, about 850 mg/g, about 900 mg/g, about 950 mg/g, up to about 1000 mg/g.

In various embodiments, the composition comprises one or more of caffeic acid phenylether ester (CAPE), caffeic acid, pinocembrin, benzyl caffeate, chrysin, galangin, and pinobanksin.

In exemplary embodiments, the composition is one to which has been added one or more of CAPE, caffeic acid, pinocembrin, benzyl caffeate, chrysin, galangin, and pinobanksin.

In one embodiment, the composition has a CAPE concentration of greater than about 1, 2, 3, 5, 10, 15, 20, 25, 30, 35, 40, 45, 50, 60, 70, 75, 80, 90, 100, 125, 150, 175, 200, 250, 300, 350, 400, 450, 500, 600, 700, 800, 900 or 999 mg/g and useful ranges may be selected between any of these values (for example, about 1 to about 5, about 1 to about 10, about 2 to about 20, about 5 to about 20, about 5 to about 25, about 10 to about 25, about 10 to about 40, about 15 to about 100, or about 20 to about 999 mg/g).

In one embodiment, the composition has a pinocembrin concentration of greater than about 1, 2, 3, 5, 10, 15, 20, 25, 30, 35, 40, 45, 50, 60, 70, 75, 80, 90, 100, 125, 150, 175, 200, 250, 300, 350, 400, 450, 500, 600, 700, 800, 900 or 999 mg/g and useful ranges may be selected between any of these values (for example, about 1 to about 5, about 1 to about 10, about 2 to about 20, about 5 to about 20, about 5 to about 25, about 10 to about 25, about 10 to about 40, about 15 to about 100, or about 20 to about 999 mg/g).

In one embodiment, the composition has a galangin concentration of greater than about 1, 2, 3, 5, 10, 15, 20, 25, 30, 35, 40, 45, 50, 60, 70, 75, 80, 90, 100, 125, 150, 175, 200, 250, 300, 350, 400, 450, 500, 600, 700, 800, 900 or 999 mg/g and useful ranges may be selected between any of these values (for example, about 1 to about 5, about 1 to about 10, about 2 to about 20, about 5 to about 20, about 5 to about 25, about 10 to about 25, about 10 to about 40, about 15 to about 100, or about 20 to about 999 mg/g).

In one embodiment, the composition has a chrysin concentration of greater than about 1, 2, 3, 5, 10, 15, 20, 25, 30, 35, 40, 45, 50, 60, 70, 75, 80, 90, 100, 125, 150, 175, 200, 250, 300, 350, 400, 450, 500, 600, 700, 800, 900 or 999 mg/g and useful ranges may be selected between any of these values (for example, about 1 to about 5, about 1 to about 10, about 2 to about 20, about 5 to about 20, about 5 to about 25, about 10 to about 25, about 10 to about 40, about 15 to about 100, or about 20 to about 999 mg/g).

In one embodiment, the composition has a pinobanksin concentration of greater than about 1, 2, 3, 5, 10, 15, 20, 25, 30, 35, 40, 45, 50, 60, 70, 75, 80, 90, 100, 125, 150, 175, 200, 250, 300, 350, 400, 450, 500, 600, 700, 800, 900 or 999 mg/g and useful ranges may be selected between any of these values (for example, about 1 to about 5, about 1 to about 10, about 2 to about 20, about 5 to about 20, about 5 to about 25, about 10 to about 25, about 10 to about 40, about 15 to about 100, or about 20 to about 999 mg/g).

In one embodiment, the composition has a caffeic acid concentration of greater than about 1, 2, 3, 5, 10, 15, 20, 25, 30, 35, 40, 45, 50, 60, 70, 75, 80, 90, 100, 125, 150, 175, 200, 250, 300, 350, 400, 450, 500, 600, 700, 800, 900 or 999 mg/g and useful ranges may be selected between any of these values (for example, about 1 to about 5, about 1 to about 10, about 2 to about 20, about 5 to about 20, about 5 to about 25, about 10 to about 25, about 10 to about 40, about 15 to about 100, or about 20 to about 999 mg/g).

In various embodiments, the composition comprises or is administered separately, simultaneously or sequentially with at least one additional therapeutic agent, preferably the at least one additional therapeutic agent is an anti-tumour agent, preferably the anti-tumour agent is selected from an anti-tumour food factor, a chemotherapeutic agent, or an immunotherapeutic agent.

In various embodiments, the gastrointestinal cancer therapy, the therapeutic agent, or the anti-tumour agent is effective to induce apoptosis, for example, induce apoptosis in one or more gastrointestinal cancer cells or in one or more neoplastic cells.

In one embodiment, the gastrointestinal cancer therapy, the therapeutic agent, or the anti-tumour agent is butyrate or a source of butyrate.

In a further embodiment, the butyrate is generated by the digestion of cyclodextrin by intestinal or colonic microflora.

In one embodiment, the composition is a consumer good.

In one embodiment the composition is a food, drink, food additive, drink additive, dietary supplement, nutritional product, medical food, nutraceutical, medicament or pharmaceutical.

In various embodiments, the composition may be formulated for oral, topical, or parenteral administration.

In one embodiment, the composition comprises one or more additional anti-gastrointestinal cancer agents.

In one embodiment, the composition is a pharmaceutical composition.

In various embodiments, the chemotherapeutic agent is selected from the group comprising mitotic inhibitors, such as *vinca* alkaloids, including vincristine, vinblastine, vinorelbine, vindesine, vinflunine, podophyllotoxin, taxanes, including docetaxel, larotaxel, ortataxel, paclitaxel, and tesetaxel, and epothilones, such as ixabepilone; topoisomerase I inhibitors, such as topotecan, irinotecan, camptothecin, rubitecan, and belotecan, topoisomerase type II inhibitors, including amsacrine, etoposide, etoposide phosphate, and teniposide, anthracyclines, such as aclarubicin, daunorubicin, doxorubicin, epirubicin, idarubicin, amrubicin, pirarubicin, valrubicin, and zorubicin, and anthracenediones, such mitoxantrone and pixantrone; antimetabolites, including dihydrofolate reductase inhibitors, such as aminopterin, methotrexate, pemetrexed, thymidylate synthase inhibitors, such as raltitrexed and pemetrexed, adenosine deaminase inhibitors, including pentostatin, halogenated or ribonucleotide reductase inhibitors, such as cladribine, clofarabine, and fludarabine, thiopurines, including thioguanine and mercaptopurine, thymidylate synthase inhibitors, including fluorouracil, capecitabine, tegafur, carmofur, and floxuridine, DNA polymerase inhibitors, such as cytarabine, ribonucleotide reductase inhibitors, such as gemcitabine, hypomethylating agents, including azacitidine, and decitabine, and ribonucleotide reductase inhibitors, such as hydroxyurea; cell-cycle nonspecific antineoplastic agents, including alkylating agents such as nitrogen mustards, including mechlorethamine, cyclophosphamide, ifosfamide, trofosfamide, chlorambucil, melphalan, prednimustine, bendamustine, uramustine, estramustine, nitrosoureas, including carmustine, lomustine, semustine, fotemustine, nimustine, ranimustine, and streptozocin, alkyl sulfonates, including busulfan, mannosulfan, and treosulfan, aziridines, including carboquone, thioTEPA, triaziquone, and triethylenemelamine, alkylating-like agents, including platinum agents such as cisplatin, carboplatin, oxaliplatin, nedaplatin, triplatin tetranitrate, satraplatin, hydrazines, such as procarbazine, triazenes, such as dacarbazine, temozolomide, altretamine, and mitobronitol, and streptomycins, such as actinomycin, bleomycin, daunomycin, mitomycin, and plicamycin; photosensitizers, including aminolevulinic acid, methyl aminolevulinate, efaproxiral, and porphyrin derivatives, such as porfimer sodium, talaporfin, temoporfin, and verteporfin; enzyme inhibitors, including farnesyltransferase inhibitors such as tipifarnib, cyclin-dependent kinase inhibitors, such as alvocidib and seliciclib, proteasome inhibitors, such as bortezomib, phosphodiesterase inhibitors, such as anagrelide, IMP dehydrogenase inhibitors, such as tiazofurine, lipoxygenase inhibitors, such as masoprocol, and PARP inhibitors, such as olaparib; receptor antagonists, such as endothelin receptor antagonists including atrasentan, retinoid X receptor antagonists, such as bexarotene, and testolactone; and other chemotherapeutics, including amsacrine, trabectedin, retinoids such as alitretinoin and tretinoin, arsenic trioxide, asparagine depleters such as asparaginase or pegaspargase, celecoxib, demecolcine, elesclomol, elsamitrucin, etoglucid, and lonidamine.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The invention may also be said broadly to consist in the parts, elements and features referred to or indicated in the specification of the application, individually or collectively, in any or all combinations of two or more of said parts, elements or features, and where specific integers are mentioned herein that have known equivalents in the art to which the invention relates, such known equivalents are deemed to be incorporated herein as if individually set forth.

BRIEF DESCRIPTION OF THE FIGURES

FIG. 1A In this graphic, taller bars represent higher activity of the fraction in the assay (% inhibition), and vice versa. FIG. 1B This graph presents % Efficacy for samples comprising propolis (wherein % Efficacy=% Inhibition/propolis concentration), and % Inhibition for the identified samples, as described in Example 1.

DETAILED DESCRIPTION

Figure 1A:
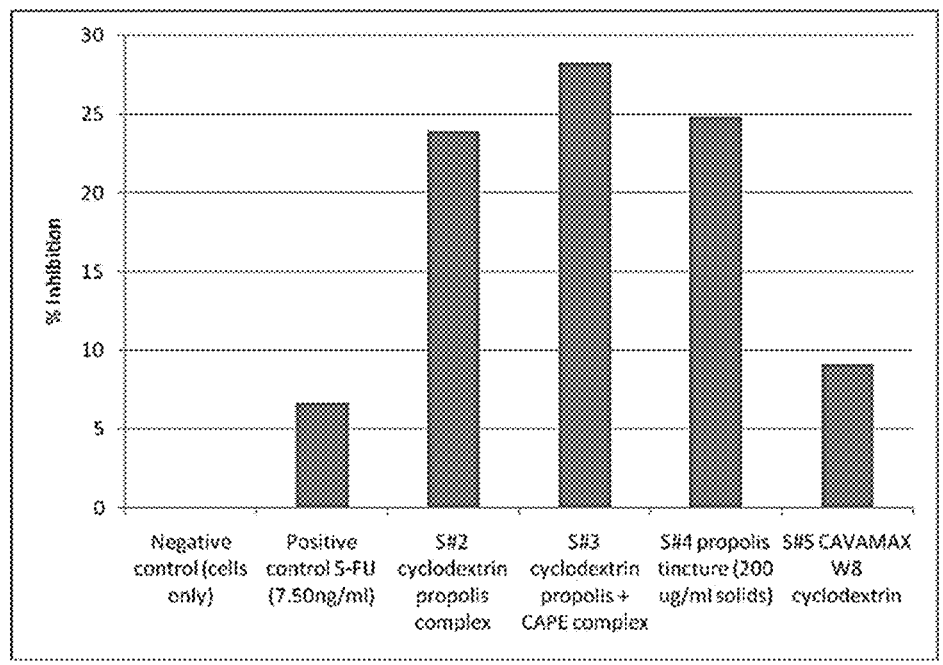
FIG. 1A and FIG. 1B. Graphic showing summarised data for the DLD-1 assay using European propolis-cyclodextrin complex, CAPE-enriched European propolis-cyclodextrin, European propolis tincture and unmodified cyclodextrin as described in Example 1.

The present invention is based on the finding that compositions comprising propolis and cyclodextrin; and particularly gamma cyclodextrin, for example compositions comprising European propolis and gamma-cyclodextrin, have anti-gastrointestinal cancer efficacy, including enhanced efficacy, and preventative activity. The pharmaceutical compositions of the invention, for example the anti-gastrointestinal cancer compositions of the invention, enhance the activity and physicochemical properties of propolis. The nutraceutical compositions of the invention, for example the gut health compositions of the invention also enhance the activity and physicochemical properties of the propolis present in the composition.

Accordingly, provided that the anti-gastrointestinal cancer compositions are formulated so as to be suitable for administration to a mammalian subject, for example they consist of materials that are safe to the human body, they can be used for manufacturing anti-gastrointestinal cancer pharmaceutical compositions and drugs, as well as nutraceutical compositions, consumer goods, such as beverages, foods, and the like.

Furthermore, as the anti-gastrointestinal cancer activity of embodiments of the compositions of the invention is maintained for a sustained period, the dosage or frequency of administration of the composition can be reduced, or higher efficacy is provided, or both.

The phrases "anti-gastrointestinal cancer compositions" or "compositions having anti-gastrointestinal cancer activity" (used interchangeably herein) of this invention contemplate any kind of compositions. Examples include anti-gastrointestinal cancer compositions containing propolis and cyclodextrin or anti-gastrointestinal cancer compositions containing materials with propolis contained and cyclodextrin. Synergistic compositions which enhance any anti-gastrointestinal cancer activity observed in either propolis or in cyclodextrin alone are particularly contemplated. The anti-gastrointestinal cancer compositions may be anti-colorectal cancer, anti-gastric cancer or anti-throat cancer compositions.

The term "and/or" can mean "and" or "or".

The terms "cancer" and "cancerous" refer to a physiological condition in mammals that is typically characterized by abnormal or unregulated cell proliferation, cell survival, cell motility, neoplasticity, and/or oncogenicity. Cancer and cancer pathology can be associated, for example, with metastasis, interference with the normal functioning of neighbouring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc. Specifically included are colorectal cancers, gastric cancers, throat cancers and precancerous conditions, which can include epithelial tumours, nonepithelial tumours, carcinomas, adenocarcinomas, gastric lymphomas, carcinoid tumours, stromal tumours or squamous cell carcinomas for example, carcinomas in situ, as well as invasive colorectal, gastric or throat cancers.

The term "comprising" as used in this specification means "consisting at least in part of". When interpreting statements in this specification that include that term, the features, prefaced by that term in each statement, all need to be present but other features can also be present. Related terms such as "comprise" and "comprised" are to be interpreted in the same manner.

An "effective amount" is the amount required to confer therapeutic effect. The interrelationship of dosages for animals and humans (based on milligrams per meter squared of body surface) is described by Freireich, et al. (1966). Body surface area can be approximately determined from height and weight of the subject. See, e.g., Scientific Tables, Geigy Pharmaceuticals, Ardley, N.Y., 1970, 537. Effective doses also vary, as recognized by those skilled in the art, dependent on route of administration, excipient usage, and the like.

As used herein, an "extract" or a "fraction" of propolis are suitable for use in the present invention provided they at least retain one or more anti-gastrointestinal cancer activity exhibited by propolis. Such functional extracts or functional fractions may have greater or lesser activity than the crude propolis. In one example, one or more of the biological activities of the crude propolis possessed by the functional extract or functional fraction may be present to a greater or lesser degree in the functional extract or functional fraction than is found in the crude propolis. In another example, each of the biological activities of the crude propolis possessed by the functional extract or functional fraction is present to a greater or lesser degree in the functional extract or functional fraction than is found in the crude propolis. In still a further example, it may be desirable to provide a functional extract or functional fraction in which one or more of the biological activities of the crude propolis is maintained or is present to a greater degree than is found in the crude propolis, but one or more other biological activities of the crude propolis is not present or is present to a lesser degree than is found in the crude propolis. Examples of such functional extracts include the anti-gastrointestinal cancer tincture described herein in the Examples.

Methods and assays to determine one or more biological effects elicited by propolis are well known in the art and examples are described herein, and such methods and assays can be used to identify or verify one or more functional extracts or functional fractions of propolis. For example, an assay of the ability of propolis to increase one or more oncogenic traits in a cell, such as those described herein in the Examples, is amenable to identifying one or more functional extracts or functional fractions of propolis.

As used herein, "propolis" contemplates propolis produced by bees from any botantical source. In one embodiment, the propolis is "European" propolis. "European" propolis is also known under different names, such as "Poplar" propolis. For example, the propolis is derived principally from the bud and leaf exudates of one or more species of poplars, and to a lesser extent birches, larches or willows. Propolis has been classified into seven major classes based on plant source (Sforcin and Bankova, 2011. Propolis: is there a potential for the development of new drugs? J. Ethnopharmacology, 133: 253-260.). These classes are "Poplar" from Europe, North America, Southern South America, New Zealand; "Brazilian green", which contains artepillan C; "Birch" from Russia; "Red propolis" from Cuba, Brazil, Mexico; "Mediterranean" from Greece, Sicily, Crete, Malta rich in diterpenes that are sourced from conifers; "Clusia" from Cuba and Venezuela; and "Pacific" from Okinawa, Taiwan, Indonesia, which contain 'propolins'.

Exemplary compounds and concentrations of the compounds reported in European type propolis from various countries are presented in Table 1 below, along with a comparative example of Brazilian green propolis. These compounds are useful, for example in identifying the source of propolis as being a European-type propolis, or in characterizing and identifying propolis suitable for use in the present invention. It has been reported that Brazilain green propolis contains none of the flavoinoid and caffeic acid ester compounds characteristic of European-type propolis

TABLE 1

Compositional data for ethanol soluble extract of propolis from various geographic regions (adapted from Kumazawa et al., 2004 Identification of metabolites in plasma and urine of Uruguayan propolis-treated rats. Journal of Agricultural and Food Chemistry 52(10): 3083-3088.)

|  | Arg | Aus | Bra | Bul | Chil | Chi a | Chi b | Chi c | Hun | SA | Ukr | Uru | USA | Uzb | NZ | MHNZ1 | MHNZ2 |
|---|---|---|---|---|---|---|---|---|---|---|---|---|---|---|---|---|---|
| Caffeic acid | 0.7 | 1.7 | 1.6 | 7.2 | 0.4 | 3.3 | 2.8 | 2.4 | 3.1 | 0.2 | 0.8 | 0.7 | 0.8 | 1.5 | 2.8 | 9.4 | 7.2 |
| p-Coumaric | 1.8 | 3.6 | 27.4 | 3.5 | 1.9 | 4 | 4 | 3 | 3.7 | 1.5 | 8.9 | 8.4 | 19.4 | 0.9 | 3.1 | 3.4 | 2.6 |
| 3,4-Dimethoxy cinnamic acid | 2.2 | 8.6 |  | 4 | 1.8 | 10.1 | 7.4 | 7.9 | 5.2 |  | 0.8 | 1.1 | 2 | 2.6 | 9.2 | NQbp | NQbp |
| Quercetin | 2.2 | 4.8 |  | 4.7 | 1.5 | 4.4 | 3.8 | .8 | 4.4 |  |  | 2.5 | 3.8 | 0.8 | 1.2 |  |  |
| ksin-5-methyl | 15 | 23.8 |  | 19.7 | 18.8 | 19.8 | 26.2 | 21.1 | 21.8 | 5.9 | 7.5 | 51 | 23.8 | 10.8 | 20 |  |  |
| Apigenin | 12 | 18.4 |  | 13.4 | 14.2 | 17.1 | 17.1 | 14.3 | 9 |  | 3.9 | 14.8 | 0.6 | 8.1 | 78.3 |  |  |
| Kaemferol | 2.3 | 3.9 |  | 5 | 1.4 | 2.1 | 2.6 | 2.5 | 4.8 | 1 | 10.9 | 2.5 | 10.3 | 3.8 | 3.7 |  |  |
| Pinobanksin | 22.5 | 32.1 |  | 84.8 | 21.4 | 36.1 | 35 | 22.5 | 21.3 | 31.4 | 6.6 | 36.5 | 23.2 | 29.4 | 36.3 | 35.2 | 25 |
| Cinnamylidene-a[1] | 30.4 | 14.6 |  | 6.3 | 31.2 | 11.2 | 12.7 | 10.5 | 7.8 |  |  | 13.7 | 5.2 | 2.9 | 18.1 | NQbp | NQbp |

TABLE 1-continued

Compositional data for ethanol soluble extract of propolis from various geographic regions (adapted from Kumazawa et al., 2004 Identification of metabolites in plasma and urine of Uruguayan propolis-treated rats. Journal of Agricultural and Food Chemistry 52(10): 3083-3088.)

| | Arg | Aus | Bra | Bul | Chil | Chi a | Chi b | Chi c | Hun | SA | Ukr | Uru | USA | Uzb | NZ | MHNZ1 | MHNZ2 |
|---|---|---|---|---|---|---|---|---|---|---|---|---|---|---|---|---|---|
| Chrysin | 68.5 | 139 | | 120 | 66.3 | 127.3 | 138 | 138 | 82.9 | 11.2 | 12.9 | 77.3 | 39.4 | 87 | 102 | 32.9 | 24.9 |
| Pinocembrin | 68.7 | 58.7 | | 94.4 | 86.2 | 54.8 | 61.5 | 46.9 | 51.2 | 69.8 | 9.2 | 75 | 46.7 | 44.5 | 100 | 119 | 95.7 |
| Galangin | 32.5 | 42.5 | | 45.6 | 37.7 | 39.6 | 33.5 | 32.6 | 44.2 | 18.9 | 13.4 | 48.8 | 21.5 | 41.4 | 58.2 | 50.6 | 37.3 |
| Pinobanksin-3-acetate | 56.3 | 79.7 | | 41.2 | 63.4 | 52.5 | 64.2 | 51.2 | 59.9 | 7.7 | 14.7 | 80 | 27.6 | 58.4 | 66.2 | 71.3 | 65.5 |
| CAPE | 8.6 | 10.4 | | 5.6 | 7.4 | 29.2 | 24.5 | 19.3 | 15.4 | | 2.6 | 12.4 | 7.2 | 18.6 | 12 | 9.4 | 6.1 |
| Cinnamyl caffeate | 6.6 | 16.6 | | 0.7 | 6.1 | 16.3 | 20.3 | 14.4 | 13.8 | | 2.1 | 8.9 | 7.5 | 2.2 | 12.7 | NQbp | NQbp |
| Tectochrysin | 31.4 | 58.2 | | 96.9 | 33.1 | 62 | 45.4 | 35.5 | 39.0 | 7.7 | 12.4 | 23.8 | 36.1 | 7.3 | 62.2 | 3.5 | 3.3 |
| Artepillin-c | | | 43.9 | | | | | | | | | | | | | | |

All values are mg/g propolis resin.
NQbp = Not quantified but present
[1]Cinnamylideneacetic acid (or phenyl petadienoic acid).
Arg = Argentina, Aus = Australia, Bra = Brazilian green? propolis, Bul = Bulgaria, Chil = Chile, Chi = Chinese (a = Hebei, b = Hubei and c = Zheijiang province), Hun = Hungary, NZ = New Zealand, SA = South Africa, Ukr = Ukraine, Uru = Uruguay, Uzb = Uzbekistan, MHNZ 1 = New Zealand propolis (Manuka Health NZ Ltd), MHNZ 2 = New Zealand propolis (Manuka Health NZ Ltd).

As will be appreciated by those skilled in the art, the identity, and in certain cases the suitability for particular uses, including use in the present invention, of propolis may be determined by analysis of the composition of the propolis. The presence and amount of specific compounds, (including the compounds discussed herein)—frequently referred to as "marker compounds", allows a determination of the suitability of a particular source of propolis, for example European propolis compared to Brazilian propolis, for a particular use. In certain embodiments of the present invention, the presence or amount of one or more marker compounds is assayed, as a preliminary grading step, prior to formulation of the composition of the invention.

When used in respect of an agent having anti-gastrointestinal cancer activity, such as a composition of the invention or a component of a composition of the invention, the phrase "retaining anti-gastrointestinal cancer activity" and grammatical equivalents and derivatives thereof is intended to mean that the agent still has useful anti-gastrointestinal cancer activity. Preferably, the retained activity is at least about 35, 40, 45, 50, 55, 60, 65, 70, 75, 80, 85, 90, 95, 99 or 100% of the original activity, and useful ranges may be selected between any of these values (for example, from about 35 to about 100%, from about 50 to about 100%, from about 60 to about 100%, from about 70 to about 100%, from about 80 to about 100%, and from about 90 to about 100%). Exemplary compositions of the invention are capable of supporting the maintenance of useful anti-gastrointestinal cancer activity of the anti-gastrointestinal cancer agent (s) they comprise, and can be said to retain anti-gastrointestinal cancer activity, ideally until utilized in the methods contemplated herein.

When used in respect of a composition of the invention or a component of a composition of the invention, the phrase "enhancing anti-gastrointestinal cancer activity" and grammatical equivalents and derivatives thereof is intended to mean that when present in the composition, an equivalent amount or concentration of the anti-gastrointestinal cancer agent has increased anti-gastrointestinal cancer activity compared to that of the agent in the absence of the composition (such as the isolated agent). Preferably, the enhanced activity is at least about 105, 110, 115, 120, 125, 130, 135, 140, 145, 150, 155, 160, 165, 170, 175, 180, 185, 190, 195, 200%, or more of the original activity, and useful ranges may be selected between any of these values (for example, from about 105 to about 200%, from about 120 to about 200%, from about 140 to about 200%, from about 150 to about 200%, from about 180 to about 200%, and from about 190 to about 200%). In certain embodiments, compositions of the invention may exhibit enhanced anti-gastrointestinal cancer activity, that is, exhibit at least about 105, 110, 115, 120, 125, 130, 135, 140, 145, 150, 155, 160, 165, 170, 175, 180, 185, 190, 195, 200%, or more of the anti-gastrointestinal cancer activity of propolis alone, or of cyclodextrin alone. Similarly, preferred compositions of the invention are capable of supporting the maintenance of enhanced anti-gastrointestinal cancer activity, and can be said to retain enhanced anti-gastrointestinal cancer activity, ideally until utilised using the methods contemplated herein. The enhanced activity (including enhanced maintenance of activity) is believed, without wishing to be bound by any theory, to result from synergy amongst the various components of the compositions of the invention.

As used herein, the term "stable" when used in relation to a composition of the invention means a composition capable of supporting anti-gastrointestinal cancer activity for preferably more than two hours, more than three hours, 6 hours, 9 hours, 12 hours, 15 hours, 18 hours, 20 hours, more than one day, preferably about two, about three, about four, preferably about five, more preferably about six days, preferably a week, two weeks, three weeks, a month, or longer. It will be appreciated that in certain embodiments, stable compositions include those which have anti-gastrointestinal cancer activity for a period greater than does the propolis or cyclodextrin alone.

The term "oral administration" includes oral, buccal, enteral and intra-gastric administration.

The term "parenteral administration" includes but is not limited to topical (including administration to any dermal, epidermal or mucosal surface), subcutaneous, intravenous, intraperitoneal, intramuscular and intratumoural (including any direct administration to a tumour) administration.

The term "pharmaceutically acceptable carrier" is intended to refer to a carrier including but not limited to an excipient, diluent or auxiliary that can be administered to a subject as a component of a composition of the invention. Preferred carriers do not reduce the activity of the composition and are not toxic when administered in doses sufficient to deliver an effective amount of propolis or extracts thereof, or, when administered, of another anti-gastrointestinal cancer agent.

The term "(s)" following a noun contemplates the singular or plural form, or both.

The term "subject" is intended to refer to an animal, preferably a mammal, more preferably a mammalian companion animal or human. Preferred companion animals include cats, dogs and horses. Other mammalian subjects include an agricultural animal, including a horse, a pig, a sheep, a goat, a cow, a deer, or a fowl, or a laboratory animal, including a monkey, a rat, or a mouse.

The term "treat" and its derivatives should be interpreted in their broadest possible context. The term should not be taken to imply that a subject is treated until total recovery. Accordingly, "treat" broadly includes maintaining a subject's disease progression or symptoms at a substantially static level, increasing a subject's rate of recovery, amelioration of the onset of the symptoms or severity of a particular condition, or extending a patient's quality of life.

Exemplary Uses of the Invention

The methods and compositions of the invention may be used in the treatment or prevention of colorectal cancers, neoplastic disorders associated with colorectal cancer cells, and the symptoms of colorectal cancer, colorectal cancer treatment, and associated disorders. Colorectal cancer is a neoplastic condition affecting the large intestine, particularly the colon and rectum—hence it is commonly referred to as colon cancer or bowel cancer. Risk factors include age, diet, in particular high intake of fat, alcohol or red meat, male gender, obesity, smoking and lack of exercise.

Colorectal cancer originates from epithelial cells in the colon or rectum of the gastrointestinal tract, and is most commonly associated with defects in the Wnt-APC-beta-catenin signaling pathway. Where possible, the preferred treatment is complete surgical removal which can be curative. If metastasis has occurred and the cancer has entered the lymph nodes, the chemotherapeutic agents fluorouracil or capecitabine have been reported to increase life expectancy. Other chemotherapeutics considered for use include fluorouracil, capecitabine, UFT, leucovorin, irinotecan, or oxaliplatin, and combinations of these agents. However, where the cancer is more widespread, or when surgery is not possible, treatment generally focuses on palliative care and extension of life expectancy. Combinations of radiation and chemotherapy can be considered for rectal cancer, but radiotherapy is not typically used in colon cancer due to radio-sensitivity of the bowels.

In certain embodiments, the methods and compositions of the invention are used in the treatment or prevention of gastric cancers, neoplastic disorders associated with gastric cancer cells, and the symptoms of gastric cancer, gastric cancer treatment, and associated disorders.

Gastric cancer is a neoplastic condition arising from any part of the stomach. Prognosis is poor because most patients present with advanced disease. Risk factors include age, diet, in particular high intake of smoked foods, salted fish, cured meats and pickled vegetables, smoking, male gender and a history of autoimmune atrophic gastritis or intestinal metaplasia.

Approximately 90% of gastric cancers are adenocarcinomas, originating in the glandular epithelium of the gastric mucosa. Other types include lymphomas (MALTomas OR MALT lymphoma), and carcinoid and stromal tumours. Where possible, the preferred treatment is complete surgical removal of all or part of the stomach and surrounding lymph nodes. Gastric cancers are not particularly sensitive to chemotherapeutic agents, however, chemotherapeutics including fluorouracil, capecitabine, BCNU (carmustine), methyl-CCNU (Semustine), and doxorubicin (Adriamycin), Mitomycin C, cisplatin and taxotere have been used in palliative care regimes. Combinations of radiation and chemotherapy are sometimes used for the treatment of gastric cancers.

In certain embodiments, the invention also relates to methods of at least partially reversing the resistance of a neoplastic cell in a subject suffering from a gastrointestinal cancer to a gastrointestinal cancer therapy, or to a method of reversing, wholly or in part, the resistance of a gastrointestinal cancer-burdened patient to a gastrointestinal cancer therapy, or to a method of re-sensitising one or more tumours of a gastrointestinal cancer-burdened patient which are, or are predicted to either be or become, resistant to treatment with a gastrointestinal cancer therapy, said methods comprising the step of administering to said patient a composition comprising, consisting essentially or, or consisting of propolis and cyclodextrin.

In one embodiment, the one or more tumours are or are predicted to be or to become resistant to a gastrointestinal cancer therapy due increased activation of one or more pro-cancer cell survival signaling pathways within the one or more tumours or within the patient, including increased activation of one or more of the AKT, JNK or JAK/STAT signaling pathways, for example within a sample from the patient, such as a tissue sample, a tumour biopsy, or a blood or plasma sample.

Pro-cancer cell survival signaling pathways implicated in the onset and development of gastrointestinal cancers are known in the art.

The methods and compositions of the invention may be used in the treatment or prevention of throat cancers, neoplastic disorders associated with throat cancer cells, and the symptoms of throat cancer, throat cancer treatment, and associated disorders.

Throat cancer, also referred to as oesophaegeal cancer, pharyngeal cancer, or laryngeal cancer, encompasses tumours that develop in the tissues of the pharynx, nasopharynx, oropharynx, hypopharynx, larynx (voice box) or tonsils. Approximately 90% of throat cancers are squamous cell carcinomas originating from the mucosal lining (epithelium) of these regions. Risk factors include diet, in particular high intake of alcohol, smoking, use of smokeless tobacco, betel nut chewing and exposure to environmental carcinogens including occupational exposures nickel refining, textile fibres and woodworking.

The most common therapies are surgical excision of tumours and radiation therapy. Chemotherapeutic agents may be used in combination surgery and/or radiation. Agents include paclitaxel, carboplatin, cetuximab, taxotere and docetaxel.

The methods and compositions of the invention may also be used for maintaining or improving gut health.

Robust gut health is associated with intestinal comfort, resistance to infectious diseases and the prevention of chronic gastrointestinal diseases.

This includes the treatment or prevention of a condition associated with poor gut health, low immunity and gastrointestinal tract inflammation. For example, the methods and compositions of the invention are useful for the treatment or prevention of inflammatory bowel disease, irritable bowel syndrome, environmental enteropathy, infectious diarrhoea and for the removal or alleviation of visceral pain.

Propolis and Materials Comprising Propolis

Propolis is available in New Zealand and elsewhere, commonly as a resinous sticky solid. Propolis may be obtained from bee-hives with the resulting propolis held in storage, for example to assess the propolis content. Those skilled in the art will recognise that for use in the present invention, propolis may be processed to a form suitable for admixture, for example with cyclodextrin, while maintaining the bioactive ingredients. Typically the propolis, or an extract thereof, is processed to a fine particulate form or a concentrated tincture. Various methods of preparing active propolis, or an extract thereof, to a particulate form or concentrated tincture are known. Most commonly, crude propolis is extracted using ethanol or ethanol/water mixtures to produce a dilute tincture. Wax associated with the crude propolis is at best poorly soluble in the solvent and so is mostly not extracted. Any extracted wax can be removed by cooling the dilute tincture and then settling, filtration, or centrifugation. The tincture can then be concentrated by partial to complete evaporation of the solvent to give a concentrated tincture, optionally followed by freeze drying to give a powder. Alternatively, the tincture can be spray dried to give a powder. Fractions can be prepared by using methods known in the art such as chromatography (such as HPLC) using, for example, a size exclusion matrix or a reverse phase matrix, or supercritical fractionation. A typical solvent for use in such a chromatographic process is ethanol or another water miscible alcohol.

In one embodiment propolis or concentrated propolis tincture is combined with other compounds that enhance the properties of propolis, for example a compound that enhances the ease of formulation or administration, or that enhances anti-gastrointestinal cancer activity, or that enhances the stability of one or more anti-gastrointestinal cancer activities present in propolis. Examples of additional compounds are those that improve the therapeutic benefits of the propolis. Exemplary compositions in which one or more compounds present in propolis, and in European propolis in particular, including biologically active compounds such as CAPE, caffeic acid, pinocembrin, benzyl caffeate, chrysin, galangin, pinobanksin, and pinobanksin-3-acetate are added are specifically contemplated. In other examples, additional compounds are included to improve or maintain the physiological benefits of the composition, for example mannitol can be added to enhance the diuretic properties of the resulting composition. Alternatively or additionally other compounds such as excipients, and/or propellants could be added to improve the dosing, manufacturability or delivery properties of the composition.

In particularly contemplated embodiments, dewaxed propolis resin, optionally with one or more additional compounds added, is admixed with cyclodextrin and the admixture dried. Further processing of the admixture, for example, to obtain a particle size distribution that enables ready admixture with the other components of the composition, ease of tableting, or ease of administration to a subject, is conducted.

In typical embodiments, the propolis or propolis resin is sterilized, for example by heating to kill bacteria, protozoa, yeast, fungi and other organisms that naturally may be present in the propolis.

Cyclodextrins and Materials Comprising Cyclodextrin

Cyclodextrins are cyclic molecules composed of glucopyranose ring units which form toroidal structures. The interior of the cyclodextrin molecule is hydrophobic and the exterior is hydrophilic, making the cyclodextrin molecule water soluble. The degree of solubility can be altered through substitution of the hydroxyl groups on the exterior of the cyclodextrin. Similarly, the hydrophobicity of the interior can be altered through substitution, though generally the hydrophobic nature of the interior allows accommodation of relatively hydrophobic guests within the cavity. Accommodation of one molecule within another is known as complexation and the resulting product is referred to as an inclusion complex. Cyclodextrins are typically identified with reference to the number of monomeric units that comprise the molecule, wherein alpha-cyclodextrin (α-cyclodextrin) comprises six monomeric units, beta-cyclodextrin (β-cyclodextrin) comprises seven monomeric units, and gamma-cyclodextrin (γ-cyclodextrin) comprises eight monomeric units. Larger cyclodextrin molecules have been described, including a well-characterised cyclodextrin containing 32 1,4-anhydroglucopyranoside units Cyclodextrin molecules may conveniently be derivatised, by for example chemical modification, for example to alter one or more of the physicochemical properties thereof. Examples of cyclodextrin derivatives include methylated cyclodextrins, sulfobutylcyclodextrin, maltosylcyclodextrin, hydroxypropylcyclodextrin, and salts thereof. Those skilled in the art will recognise that various derivates of cyclodextrin may be suitable for particular purposes, for example, certain derivatives of cyclodextrin are not be acceptable for administration to human subjects, but are suitable for industrial uses.

Cyclodextrins comprising the anti-gastrointestinal cancer compositions of the present invention may be commercially available, or may be prepared independently by methods well known to those skilled in the art. It will be apparent to those skilled in the art that cyclodextrins used in the anti-gastrointestinal cancer compositions for administration to a subject, for example a cyclodextrin for manufacturing a beverage, food, or pharmaceutical of the invention should be safe to human body, and preferably is a pharmaceutically acceptable cyclodextrin.

In particularly contemplated embodiments, gamma-cyclodextrin or combinations comprising gamma-cyclodextrin are used. In such embodiments, anti-gastrointestinal cancer activity is substantially enhanced, as presented herein in the examples. Such compositions comprising gamma-cyclodextrin can be formulated to provide enhanced mouth feel or palatability, for example compositions comprising gamma-cyclodextrin and propolis exhibit a stronger tendency to mask any distasteful flavours present in the propolis.

Cyclodextrins suitable for use in the present invention can be obtained from commercial sources, or can be prepared independently by methods well known in the art, such as from starch by enzymatic conversion. In certain embodiments, CAVAMAX W8 FOOD, a gamma-cyclodextrin commercially supplied by Wacker AG, is used.

Compositions of the Invention

Exemplary anti-gastrointestinal cancer compositions of the present invention include a powder that is obtained after mixing propolis tincture with cyclodextrin, then adding water and homogenizing the composition, and then spray-drying or freeze-drying. Other exemplary anti-gastrointestinal cancer compositions of the present invention include solutions, including for example, those in which propolis tincture and cyclodextrin are mixed and then dispersed in water, those in which propolis or materials with propolis contained and cyclodextrin are independently dissolved or dispersed in water, and then admixed, for example by kneading, and further those in which propolis powder or resin is firstly dissolved in another organic solvent in which it is soluble, such as for example propylene glycol, ethyl acetate, isopropyl alcohol, and the resultant solution is admixed with cyclodextrin, then added to water, and further mixed, for example by kneading and then dried by means known in the art, such as spray or freeze-drying. In certain embodiments, anti-gastrointestinal cancer compositions prepared as powders as described above may be preferred, for example because they may maintain stronger anti-gastrointestinal cancer activity or may maintain anti-gastrointestinal cancer activity for a longer period than that of solutions of anti-gastrointestinal cancer compositions prepared as described above.

The content of propolis and cyclodextrin of the present invention can be at any level as long as the expected anti-gastrointestinal cancer activity is realized.

Without wishing to be bound by any theory, the applicants believe that the propolis in the composition will be entirely encapsulated when the molar ratio of propolis to cyclodextrin is no greater than 1:1.

In some embodiments the molar ratio of propolis to cyclodextrin may exceed 1:1 in the compositions of the invention. In such compositions the excess propolis will not be encapsulated by the cyclodextrin.

Other anti-gastrointestinal cancer substances generally known can be combined with the anti-gastrointestinal cancer compositions of this invention, depending upon the application to which the composition is to be put.

Without wishing to be bound by any theory, the applicants believe that the enhanced anti-gastrointestinal cancer activity observed in exemplary compositions of the present invention may be due at least in part to a synergy between propolis, particularly when present as propolis, and gamma-cyclodextrin. Again, without wishing to be bound by any theory, the applicants acknowledge that there may be a role of other components of the exemplary compositions, such as polyphenols present in propolis, in achieving the observed enhanced anti-gastrointestinal cancer activities.

Compositions suitable for administration to a subject may be formulated as a food, drink, food additive, drink additive, dietary supplement, nutritional product, medical food, nutraceutical, medical supply, medical device, medicament or pharmaceutical. Appropriate formulations may be prepared by an art skilled worker with regard to that skill and the teaching of this specification.

In one embodiment the present invention relates to use of propolis and gamma cyclodextrin, optionally with at least one anti-gastrointestinal cancer agent, in the manufacture of a food, drink, food additive, drink additive, dietary supplement, nutritional product, medical food, nutraceutical, medical device, medical supply, medicament or pharmaceutical. In one embodiment, the composition is formulated for oral administration. In another embodiment, the composition is formulated for parenteral, including topical, administration. In certain embodiments, the composition is for inducing apoptosis, treating or preventing a gastrointestinal cancer, maintaining or improving gut health or one or more other uses as described above.

In one embodiment the composition is in the form of a powder, a tablet, a caplet, a pill, a hard or soft capsule or a lozenge.

In one embodiment the composition is in the form of a sachet, a dispensable powder, granules, a suspension, an elixir, a liquid, a drink, or any other form that can be added to food or drink, including for example water or fruit juice. In one embodiment the composition is an enteral product, a solid enteral product or a liquid enteral product.

In one embodiment, the composition is in the form of a cream, ointment, a paste, a drop solution including eye drops or ear drops, an inhaler or as an inhalable composition, a dressing, a pad, or a spray.

In one embodiment the composition further comprises one or more constituents (such as antioxidants) which prevent or reduce degradation of the composition during storage or after administration.

In one embodiment, compositions useful herein include any edible consumer product which is able to carry one or more cyclodextrins. When the composition comprises a proteinaceous factor as the at least one additional anti-gastrointestinal cancer agent, the edible consumer product is one able to carry protein. Examples of suitable edible consumer products include baked goods, powders, liquids, confectionary products, reconstituted fruit products, snack bars, food bars, muesli bars, spreads, sauces, dips, dairy products including ice creams, yoghurts and cheeses, drinks including dairy and non-dairy based drinks (such as milk drinks including milk shakes, and yogurt drinks), milk powders, sports or nutritional supplements including dairy and non-dairy based sports or nutritional supplements, food additives such as protein sprinkles and dietary supplement products including daily supplement tablets. Within this embodiment, a composition useful herein may also be an infant formula, in powder or liquid form. Suitable nutraceutical compositions useful herein may be provided in similar forms. Particularly contemplated are compositions additionally comprising milk or one or more milk products or components of milk, such as milk protein, whey protein, colostrums, milk fat, or any fractions of milk or one or more milk products or components of milk, such as a milk fat fraction, a milk protein fraction, a whey protein fraction, a colostrums fraction, or the like.

Compositions useful herein may further include other factors such as calcium, zinc, magnesium, selenium, vitamin C, vitamin D, vitamin E, vitamin K2, complex carbohydrates, edible or cooking oils including palm, olive, soybean, canola, corn, sunflower, safflower, peanut, grape seed, sesame, nut, almond, cashew, hazelnut, macadamia, pecan, pistachio, and walnut, and other edibles include acai, amaranth, apricot, argan, artichoke, avocado, babassu, ben, blackcurrant seed, borage seed, borneo tallow nut, bottle gourd, buffalo gourd, carob pod (algaroba), cohune, coriander seed, evening primrose, false flax, hemp, kapok seed, lallemantia, meadowfoam seed, mustard, okra seed (hibiscus seed), *perilla* seed, pequi, pine nut, poppyseed, prune kernel, pumpkin seed, *quinoa*, ramtil, rice bran, tea (*camellia*), thistle, watermelon seed, or wheat germ oil, or a combination thereof.

The compositions useful herein may be formulated to allow for administration to a subject by any chosen route, including but not limited to oral or parenteral (including topical, subcutaneous, intramuscular and intravenous) administration. Those skilled in the art will appreciate that the route of administration to a subject will typically take into account the purpose for which the composition is being administered—for example, where a pharmaceutical composition of the invention is being administered to treat a microbial disease or disorder, the route of administration will typically be chosen taking into account the nature of the microbial disease or disorder.

In general, for oral administration a dietary (a food, food additive or food supplement for example), nutraceutical or pharmaceutical composition useful herein may be formulated by a skilled worker according to known formulation techniques.

Thus, a pharmaceutical composition useful according to the invention may be formulated with an appropriate pharmaceutically acceptable carrier (including excipients, diluents, auxiliaries, and combinations thereof) selected with regard to the intended route of administration and standard pharmaceutical practice. See for example, Remington's Pharmaceutical Sciences, 16th edition, Osol, A. Ed., Mack Publishing Co., 1980.

While the preferred route of administration is oral, it should be understood that any mode of administration may be suitable for any composition of the invention, including administration by multiple routes, including different routes for different agents. Therefore, inhalation (nasal or buccal inhalation) and vaginal and rectal administration of any composition of the invention is also contemplated. Intramedullar, epidural, intra-articular, and intra-pleural administration of any composition of the invention is also contemplated. Administration of a composition of the invention, optionally with at least one additional anti-gastrointestinal cancer factor, by a first administration route accompanied by separate, simultaneous or sequential administration of one or more other agents, including one or more other anti-gastrointestinal cancer agents, by a second administration route is also contemplated; for example, oral administration of a composition of the invention accompanied by topical administration of the at least one additional anti-gastrointestinal cancer agent.

The compositions of the invention may also be formulated as a dosage form. A dosage form useful herein may be administered orally as a powder, liquid, tablet or capsule. Suitable dosage forms may contain additional agents as required, including emulsifying, antioxidant, flavouring or colouring agents, or have an enteric coating. Suitable enteric coatings are known. Enteric coatings surrounding the active ingredients and prevent the release of the active ingredients in the stomach but allow release after the dosage form has left the stomach. Dosage forms useful herein may be adapted for immediate, delayed, modified, sustained, pulsed or controlled release of the active components. Suitable formulations may contain additional agents as required, including emulsifying, antioxidant, flavouring or colouring agents.

Capsules can contain any standard pharmaceutically acceptable materials such as gelatin or cellulose. Tablets can be formulated in accordance with conventional procedures by compressing mixtures of the active ingredients with a solid carrier and a lubricant. Examples of solid carriers include starch and sugar bentonite. Active ingredients can also be administered in a form of a hard shell tablet or a capsule containing a binder, e.g., lactose or mannitol, a conventional filler, and a tabletting agent. Pharmaceutical compositions can also be administered via the parenteral route. Examples of parenteral dosage forms include aqueous solutions, isotonic saline or 5% glucose of the active agent, or other well-known pharmaceutically acceptable excipient. Solubilising agents well-known to those familiar with the art, can be utilized as pharmaceutical excipients for delivery of the anti-gastrointestinal cancer agent.

Injectable dosage forms may be formulated as liquid solutions or suspensions. Solid forms suitable for solution in, or suspension in, liquid prior to injection may also be prepared. The dosage form may also be emulsified. Propolis, or a material comprising propolis, and cyclodextrin or a material comprising cyclodextrin, and when present the at least one additional anti-gastrointestinal cancer factor may be mixed with carriers such as, for example, water, saline, dextrose, glycerol, ethanol, or the like and combinations thereof.

Sustained-release preparations may be prepared incorporating propolis and cyclodextrin. Suitable examples of sustained-release preparations include semi-permeable matrices of solid hydrophobic polymers containing propolis and cyclodextrin, and when present the at least one additional anti-gastrointestinal cancer agent. The matrices may be in the form of shaped articles, e.g., films, or microcapsules. Examples of sustained-release matrices include polyesters, hydrogels (for example, poly(2-hydroxyethyl-methacrylate), or poly(vinylalcohol)), polylactides (see U.S. Pat. No. 3,773,919), copolymers of L-glutamic acid and ethyl-L-glutamate, non-degradable ethylene-vinyl acetate, and degradable lactic acid-glycolic acid copolymers such as the LUPRON DEPOT™ (injectable microspheres composed of lactic acid-glycolic acid copolymer and leuprolide acetate).

Topical formulations comprising propolis and cyclodextrin, and when present the at least one additional anti-gastrointestinal cancer agent, may be prepared as lotions, creams, ointments, pastes or salves using known carriers for such applications. Such formulations may be administered directly, for example, applied directly on to a wound, sprayed onto a surgical site, etc, or may be applied indirectly, such as by impregnation into a bandage or dressing or sprayed onto surgical equipment, dressings and the like.

The present invention also relates to a parenteral unit dosage form comprising propolis and cyclodextrin, optionally with at least one additional therapeutic agent.

In various embodiments, the at least one additional therapeutic agent is an antibiotic, such as an aminoglycoside, such as amikacin, gentamicin, kanamycin, neomycin, netilmicin, streptomycin, tobramicin, or paromomycin; an ansamycin, such as geldanamycin, or herbimycin; a carbacephem, such as loracarbef; carbapenems, such as, ertapenem, doripenem, imipenem/cilastatin, or meropenem; cephalosporins (first generation), such as cefadroxil, cefazolin, cefalotin or cefalothin, or cefalexin; cephalosporins (second generation), such as cefaclor, cefamandole, cefoxitin, cefprozil, or cefuroxime; cephalosporins (third generation), such as cefixime, cefdinir, cefditoren, cefoperazone, cefotaxime, cefpodoxime, ceftazidime, ceftibuten, ceftizoxime, or ceftriaxone; cephalosporins (fourth generation), such as cefepime; cephalosporins (fifth generation), such as ceftobiprole; glycopeptides, such as teicoplanin, or vancomycin; macrolides, such as azithromycin, clarithromycin, dirithromycin, erythromycin, roxithromycin, troleandomycin, telithromycin, or spectinomycin; monobactams, such as aztreonam; penicillins, such as amoxicillin, ampicillin, azlocillin, carbenicillin, cloxacillin, dicloxacillin, flucloxacillin, mezlocillin, meticillin, nafcillin, oxacillin, penicillin, piperacillin, or ticarcillin; polypeptides, such as bacitracin, colistin, or polymyxin b; quinolones, such as ciprofloxacin, enoxacin, gatifloxacin, levofloxacin, lomefloxacin, moxifloxacin, norfloxacin, or ofloxacin; sulfonamides, such as mafenide, sulfonamidochrysoidine (archaic), sulfacetamide, sulfadiazine, sulfamethizole, sulfanilimide (archaic), sulfasalazine, sulfisoxazole, trimethoprim, or trimethoprim-sulfamethoxazole (co-trimoxazole) (tmp-smx); tetracyclines, such as demeclocycline, doxycycline, minocycline, oxytetracycline, tetracycline; others such as arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampicin (rifampin in US), thiamphenicol, tinidazole, dapsone, clofazimine; or a cyclic lipopeptides, such as daptomycin, a glycylcycline, such as tigecycline, or an oxazolidinones, such as linezolid.

In other embodiments, the at least one additional therapeutic agent is an antifungal, such as a polyene antifungal, such as natamycin, rimocidin, filipin, nystatin, amphotericin B, candicin; imidazoles, such as miconazole, ketoconazole, clotrimazole, econazole, bifonazole, butoconazole, fenticonazole, isoconazole, oxiconazole, sertaconazole, sulconazole, or tioconazole; triazoles, such as fluconazole, itraconazole, isavuconazole, ravuconazole, posaconazole, voriconazole, or terconazole; thiazoles such as abafungin; allylamines, such as terbinafine, amorolfine, naftifine, or butenafine; echinocandins, such as anidulafungin, caspofungin, or micafungin; others such as benzoic acid, ciclopirox, tolnaftate, undecylenic acid, flucytosine or 5-fluorocytosine, griseofulvin, haloprogin, and sodium bicarbonate; or alternatives such as allicin, tea tree oil, citronella oil, iodine, lemon grass, olive leaf, orange oil, palmarosa oil, patchouli, lemon myrtle, neem seed oil, coconut oil, zinc, or selenium Alternatively the agent is selected from any of those described herein.

The efficacy of a composition useful according to the invention can be evaluated both in vitro and in vivo. See, e.g., the examples below. Briefly, in one embodiment the composition can be tested for its ability, to for example, inhibit neoplastic cell proliferation in vitro. For in vivo studies, the composition can be fed to or injected into an animal (e.g., a mouse) and its effects on gastrointestinal cancer cell survival, proliferation, metastasis, or one or more symptoms of a gastrointestinal cancer or associated disease or disorder are then assessed. Based on the results, an appropriate dosage range, frequency, and administration route can be determined.

The compositions useful herein may be used alone or in combination with one or more other anti-gastrointestinal cancer agents, or one or more additional therapeutic agents. The anti-gastrointestinal cancer agent or additional therapeutic agent may be or comprise a food, drink, food additive, drink additive, food component, drink component, dietary supplement, nutritional product, medical food, nutraceutical, medical device, medical supply, medicament or pharmaceutical. The anti-gastrointestinal cancer agent or additional therapeutic agent is preferably effective to attenuate one or more neoplastic diseases or disorders or one or more of the symptoms of one or more neoplastic diseases or disorders, or otherwise confer a benefit on the subject to whom it is administered. Preferred therapeutic agents include therapeutic food factors, immunogenic or immunostimulatory agents, wound healing agents, and the like.

It should be understood that the additional anti-gastrointestinal cancer or therapeutic agents listed above (both food based and pharmaceutical agents) may also be employed in a method according to the invention where they are administered separately, simultaneously or sequentially with a composition useful herein.

As will be appreciated, the dose of the composition administered, the period of administration, and the general administration regime may differ between subjects depending on such variables as the severity of symptoms of a subject, the type of disorder to be treated, the mode of administration chosen, and the age, sex and/or general health of a subject. However, by way of general example, from about 1 mg to about 5000 mg per kg body weight of a composition useful herein is administered, 1 mg to about 4000 mg per kg body weight of a composition useful herein is administered, 1 mg to about 3000 mg per kg body weight of a composition useful herein is administered, 1 mg to about 2000 mg per kg body weight of a composition useful herein is administered, 1 mg to about 1000 mg per kg body weight of a composition useful herein is administered, per administration or per day, preferably about 50 to about 1000 mg per kg, preferably per day. In one embodiment, the administration is of from about 0.05 mg to about 250 mg per kg body weight of a composition useful herein.

In various embodiments, sufficient composition is administered to deliver from about 0.001 mg to about 50 mg of propolis per kg body weight, from about 0.001 mg to about 40 mg of propolis per kg body weight, from about 0.001 mg to about 30 mg of propolis per kg body weight, from about 0.001 mg to about 20 mg of propolis per kg body weight, from about 0.001 mg to about 10 mg of propolis per kg body weight, from about 0.001 mg to about 5 mg of propolis per kg body weight, from about 0.001 mg to about 1 mg of propolis per kg body weight, from about 0.001 mg to about 0.5 mg of propolis per kg body weight, from about 0.001 mg to about 0.1 mg of propolis per kg body weight, or from about 0.001 mg to about 0.05 mg of propolis per kg body weight, per administration or per day.

It should be appreciated that administration may include a single dose, such as a single daily dose, or administration of a number of discrete divided doses as may be appropriate. It should be understood that a person of ordinary skill in the art will be able without undue experimentation, having regard to that skill and this disclosure, to determine an effective dosage regime (including dose and timing of administration) for a given condition.

The present invention also relates to a dietary, nutraceutical or oral pharmaceutical composition comprising, consisting essentially of or consisting of propolis or a material comprising propolis in combination with cyclodextrin. In certain embodiments the composition consists essentially of about 1 to 99 wt % propolis or a material comprising propolis and about 1 to 99 wt % cyclodextrin. For example, the composition consists essentially of about 10 to 80 wt % propolis or a material comprising propolis and about 20 to 90 wt % cyclodextrin. In another example, the composition consists essentially of about 20 to 40 wt % propolis and about 60 to 80 wt % cyclodextrin.

The present invention also relates to a dietary, nutraceutical or oral pharmaceutical composition comprising, consisting essentially of or consisting of propolis or a material comprising propolis that is encapsulated by cyclodextrin. In certain embodiments the composition consists essentially of about 1 to 30 wt % propolis or a material comprising propolis and about 70 to 99 wt % cyclodextrin. For example, the composition consists essentially of about 10 to 25 wt % propolis or a material comprising propolis and about 75 to 90 wt % cyclodextrin. In another example, the composition consists essentially of about 20 to 30 wt % propolis and about 70 to 80 wt % cyclodextrin.

In one embodiment a composition of the invention comprises propolis or a propolis fraction. In one embodiment the composition comprises at least about 1, 5, 10, 15, 20, 25, 30, 35, 40, 45, 50, 60, 70, 80, 90, or 99% by weight propolis or a propolis fraction, and useful ranges may be selected from any of these values (for example, from about 1 to about 25% by weight, from about 1 to about 30% by weight, from about 5 to about 30% by weight, from about 15 to about 30% by weight, from about 20 to about 30% by weight, from about 25 to about 30% by weight, from about 10 to about 50% by weight, from about 15 to about 50% by weight, from about 40 to about 99% by weight, from about 45 to about 99% by weight, from about 50 to about 99% by weight, from about 55 to about 99% by weight, from about 60 to about 99% by weight, from about 65 to about 99% by weight, from about 70 to about 99% by weight, from about 75 to about 99% by weight, from about 80 to about 99% by weight, from about 85 to about 99% by weight, from about 90 to about 99% by weight, or from about 95 to about 99% by weight).

In one embodiment a composition of the invention comprises cyclodextrin, preferably gamma-cyclodextrin. In one embodiment the composition comprises at least about 1, 5, 10, 15, 20, 25, 30, 35, 40, 45, 50, 55, 60, 65, 70, 75, 80, 85, 90, 95 or 99% by weight cyclodextrin, and useful ranges may be selected from any of these values (for example, from about 1 to about 99% by weight, from about 5 to about 99% by weight, from about 10 to about 99% by weight, from about 15 to about 99% by weight, from about 20 to about 99% by weight, from about 25 to about 99% by weight, from about 30 to about 99% by weight, from about 35 to about 99% by weight, from about 40 to about 99% by weight, from about 45 to about 99% by weight, from about 50 to about 99% by weight, from about 55 to about 99% by weight, from about 60 to about 99% by weight, from about 65 to about 99% by weight, from about 70 to about 99% by weight, from about 75 to about 99% by weight, from about 80 to about 99% by weight, from about 85 to about 99% by weight, from about 90 to about 99% by weight, or from about 95 to about 99% by weight).

When used in combination with another anti-gastrointestinal cancer agent or therapeutic agent, the administration of a composition useful herein and the other anti-gastrointestinal cancer agent or therapeutic agent may be simultaneous or sequential. Simultaneous administration includes the administration of a single dosage form that comprises all components or the administration of separate dosage forms at substantially the same time. Sequential administration includes administration according to different schedules, preferably so that there is an overlap in the periods during which the composition useful herein and other therapeutic agent are provided.

Additionally, it is contemplated that a composition in accordance with the invention may be formulated with additional active ingredients which may be of benefit to a subject in particular instances. For example, therapeutic agents that target the same or different facets of the disease process may be used.

Accordingly, "foods and beverages comprising anti-gastrointestinal cancer compositions" of this invention can be used for general foods and health food. Since the anti-gastrointestinal cancer compositions of the present invention mask the taste of propolis, they can be eaten as they are or in the form of powder. They can be used as an ingredient or raw material for cake, biscuit, cookie, chocolate, sweets and other confectionary, including drops or chewing gum. The compositions of the invention may be added to water as a drink, can be used as sweetener for beverages such as milk, tea, coffee, hot chocolate, etc., and as an ingredient or raw material for fruit juice beverages, sports drink, etc.

Exemplary anti-gastrointestinal cancer compositions of the invention, and methods for preparing such compositions will now be described with reference to the following examples.

EXAMPLES

Example 1

This example describes the preparation and characterization of compositions of the invention comprising propolis and cyclodextrin.

Complex CD1

A propolis-γ cyclodextrin complex comprising 27% by mass propolis solids was made using an ethanolic tincture of propolis comprising 23.1% by weight propolis solids (wax free, supplied by Manuka Health). 6.16 kg of γ cyclodextrin (CAVAMAX W8, supplied by Wacker AG) was mixed with 9.50 kg of propolis tincture in a stainless steel tank by hand until a homogenous, pasty brown liquid was obtained. 12.3 kg of water was then added in 4 steps and then the resultant mixture was homogenized at 6000 rpm for 1 hour. A further 30.43 kg of water was then added in 4 steps with continuous stirring. This solution was then spray dried to give a fine yellow powder. The flavonoid and hydroxycinnamic acid content of the complex CD1 is shown in Table 2.

Complex CD2

The same procedure for complex CD1 was used to manufacture a propolis-γ cyclodextrin complex with added CAPE, but with the following modification. 12 g of solid CAPE (supplied by Sigma Aldrich at >97% purity) was mixed with 9.5 kg of propolis containing 23.1% by weight solids until fully dissolved. The propolis tincture with added CAPE was then mixed with γ cyclodextrin, and then water, and then spray dried as above. The flavonoid and hydroxycinnamic acid content of the complex CD2 is shown in Table 2. This composition comprises twice the concentration of CAPE as Complex CD1.

Complex CD3

A propolis-γ cyclodextrin complex comprising 24% by mass propolis solids was made using an ethanolic tincture of propolis comprising 25.0% by weight propolis solids (wax free, supplied by Manuka Health). 300 g of γ cyclodextrin (CAVAMAX W8, supplied by Wacker AG) was mixed with 375 g of propolis tincture in a glass vessel by hand until a homogenous, pasty brown liquid was obtained. 1350 g of water was then added in 4 steps, and then the resultant mixture was homogenized at 6000 rpm for 1 hour. The solution was then added to a freeze drier tray, and placed in front of a forced fan until 600 g of mass was lost by evaporation. The residual solution was then frozen overnight before freeze-drying to give a light yellow, easily crushable powder. The flavonoid and hydroxycinnamic acid content of the complex CD3 is shown in Table 2.

Complex CD4

A propolis-γ cyclodextrin complex comprising 19% by mass propolis solids was made using a propylene glycol solution of propolis comprising 19% by weight propolis solids (wax free, supplied by Manuka Health). 300 g of γ cyclodextrin (CAVAMAX W8, supplied by Wacker AG) was mixed with 1350 g of water at 60° C. until fully dissolved. 375 g of propylene glycol solution of propolis was gradually added to the mixture with continuous stirring. The mixture was stirred for a further hour at 60° C. at high speed after all solution was added. The solution was then poured onto a freeze-drier tray, air cooled to room temperature, and then frozen overnight before being freeze-dried to give a yellow, easily crushable powder. The flavonoid and hydroxycinnamic acid content of the complex CD4 is shown in Table 2.

Complex CD5:

A propolis-γ cyclodextrin complex comprising 29% by mass propolis solids was made using an ethanolic tincture of propolis comprising 50.0% by weight propolis solids (wax free, supplied by Manuka Health). 7 kg of concentrated propolis tincture was mixed in steps in a stainless steel bowl with 9.5 kg of γ cyclodextrin (CAVAMAX W8, supplied by Wacker AG). When all the tincture had been added to the cyclodextrin, the resultant paste was mixed for a further hour using a whisk attachment on a planetary mixer. 50.1 kg of water was then added in 4 steps to give a yellow coloured solution. When all the water was added the solution was then stirred for a further hour. The solution was then weighed onto freeze drier trays, and then placed in a blast freezer.

When the tray contents were fully frozen, the trays were transferred to a freeze drier and then freeze-dried to give a yellow, easily crushable powder. The flavonoid and hydroxycinnamic acid content of the complex CD5 is shown in Table 2.

Complex CD6:

A propolis-γ cyclodextrin complex containing 21% by mass propolis solids was made using an ethanolic tincture of propolis containing 40.3% by weight propolis solids (wax free, supplied by Manuka Health). 6.35 kg of concentrated propolis tincture was slowly and continuously added to a stainless steel bowl containing 8.13 kg of γ cyclodextrin (CAVAMAX W8, supplied by Wacker AG) whilst stirring with a K-type mixer attached to a planetary mixer. When all the tincture had been added to the cyclodextrin, the resultant paste/powder was mixed for a further ½ hour. The paste was then removed from the bowl, the stirrer changed to a whisk, and then 60.0 kg of water was added to the bowl. Mixing was restarted, and the paste/powder was semi-continuously added. When all the paste/powder was added the solution was then stirred for a further hour. The resultant dispersion was transferred into trays, which were then heated overnight at 40° C. to drive off some water and to also induce settling of the encapsulated propolis as a pasty precipitate. The dilute solution was then carefully poured off the top of the trays, the paste was then weighed onto freeze drier trays, and these trays were then placed in a blast freezer. When the tray contents were fully frozen, the trays were transferred to a freeze drier and then freeze-dried to give a yellow, easily crushable powder. The flavonoid and hydroxycinnamic acid content of the complex CD6 is shown in Table 2.

Complex CD7:

A propolis-α cyclodextrin complex containing around 22% by mass NZ propolis solids was made using an ethanolic tincture of propolis containing 40.3% by weight propolis solids (wax free, supplied by Manuka Health). 10.91 g of concentrated propolis tincture was mixed in steps by hand in a stainless steel bowl with 12.92 g of a cyclodextrin (CAVAMAX W6, supplied by Wacker AG). When all the tincture had been added to the cyclodextrin, the resultant paste was mixed for a further ½ hour. 96.3 g of water was then added 4 steps by mixing the contents of the stainless steel bowl using a whisk attachment on a lab scale food mixer. When all the water was added the solution was then stirred for a further hour. The bulk of the well mixed solution was then added to a glass round-bottom flask, which was then manually rotated in an acetone-dry ice bath until the flask contents were fully frozen. The flask was then transferred to a lab scale freeze drier and then freeze-dried to give a light yellow, easily crushable powder. The flavonoid and hydroxycinnamic acid content of the complex CD7 is shown in Table 2.

Complex CD8:

A propolis-β cyclodextrin complex containing around 22% by mass NZ propolis solids was made using an ethanolic tincture of propolis containing 40.3% by weight propolis solids (wax free, supplied by Manuka Health). 10.06 g of concentrated propolis tincture was mixed in steps by hand in a stainless steel bowl with 12.81 g of a cyclodextrin (supplied by Sigma Chemicals). When all the tincture had been added to the cyclodextrin, the resultant paste was mixed for a further ½ hour. 98.4 g of water was then added 4 steps by mixing the contents of the stainless steel bowl using a whisk attachment on a lab scale food processor. When all the water was added the solution was then stirred for a further hour. The bulk of the well mixed solution was then added to a glass round-bottom flask, which was then manually rotated in an acetone-dry ice bath until the flask contents were fully frozen. The flask was then transferred to a lab scale freeze drier and then freeze-dried to give a light yellow, easily crushable powder. The flavonoid and hydroxycinnamic acid content of the complex CD8 is shown in Table 2.

Complex CD9:

A propolis-γ cyclodextrin complex containing around 20% by mass Brazilian green propolis solids was made using a propylene glycol solution of propolis containing 40.0% by weight propolis solids (wax free, supplied by Polenectar, Brazil). 8.13 g of γ cyclodextrin (CAVAMAX W8, supplied by Wacker AG) was dissolved into 60.0 g of water in a stainless steel bowl of a lab scale food processor. When the cyclodextrin was fully dissolved, 6.35 g of the propylene glycol solution of Brazilian green propolis was added drop wise to the solution with stirring using a whisk attachment on the lab scale food processor. When all the propolis solution was added the solution was then stirred for a further ½ hour. The bulk of the well mixed solution was then added to a glass round-bottom flask, which was then manually rotated in an acetone-dry ice bath until the flask contents were fully frozen. The flask was then transferred to a lab scale freeze drier and then freeze-dried to give a light green, easily crushable powder. The flavonoid and hydroxycinnamic acid content of the complex CD9 is shown in Table 2.

TABLE 2

CAPE and flavonoid composition of cyclodextrin complexes, mg/g of complex

| Complex | CAPE | pinobanksin | pinobanksin-3-acetate | pinocembrin | chrysin | galangin |
|---|---|---|---|---|---|---|
| CD1 | 2.0 | 5.2 | 14.6 | 19.5 | 5.4 | 8.1 |
| CD2 | 4.9 | 5.1 | 14.4 | 19.1 | 5.3 | 7.9 |
| CD3 | 1.6 | 6.4 | 17.5 | 25.4 | 6.6 | 10.1 |
| CD4 | 1.1 | 4.0 | 10.0 | 14.6 | 4.3 | 6.0 |
| CD5 | 1.7 | 6.6 | 17.2 | 24.4 | 8.5 | 10.1 |
| CD6 | 1.2 | 5.0 | 9.1 | 17.7 | 5.7 | 8.1 |
| CD7 | 1.5 | 5.7 | 10.0 | 21.0 | 6.5 | 9.2 |
| CD8 | 1.4 | 5.3 | 9.6 | 20.2 | 6.3 | 8.9 |

Example 2

This example describes an assessment of the anti-colon cancer efficacy of compositions of the present invention. This study was performed using proliferation assays in the colon cancer adenocarcinoma cell line, DLD-1.

Materials and Methods

Test samples shown below in Table 3 were assessed for their ability to modulate the viability and proliferation of human colorectal adenocarcinoma cells (DLD-1) as assessed by the MTT assay. A positive control, 5-Fluorouracil (5-FU) was included in addition to an unsupplemented cell control (negative control) in the study. All samples were normalized to 200 µg/ml total solids.

Thus, DLD-1 colon cancer cells were exposed to:

a tincture originally containing 25% solids by mass propolis which then diluted in the test solution to give 200 µg/ml total solids. The tincture was used to manufacture the cyclodextrin-encapsulated propolis samples.

Cyclodextrin propolis (γ-cyclodextrin encapsulated with 25% propolis tincture), CD1 from Table 2 in Example 1

Cyclodextrin propolis+CAPE (γ-cyclodextrin encapsulated 25% propolis tincture with added CAPE to double the concentration of CAPE relative to the tincture), CD2 from Table 2 in Example 1

γ-cyclodextrin alone (CAVAMAX W8 food gamma cyclodextrin)

5-flurorouracil at 7.50 ng/ml as a positive control

All cyclodextrin-encapsulated samples and γ-cyclodextrin alone were assayed on a per weight of sample, and so contain at most 50 µg/ml total solids as propolis.

TABLE 3

Test Samples

| Sample No | Test Sample ID |
| --- | --- |
| #2 | CD1 Cyclodextrin Propolis Complex |
| #3 | CD2 Cyclodextrin propolis + added CAPE Complex |
| #4 | 25% Propolis Tincture |
| #5 | CAVAMAX W8 Food gamma-cyclodextrin |

Description of Test Materials and Test Methods

Human colorectal adenocarcinoma epithelial cell lines were revived from cryostorage and cultured in the presence of the test and reference samples. The culture conditions for the cells were those described by the supplier of the cells (ATCC). An MTT assay was then performed on the cultures to determine the effect of the samples on the cell proliferation.

The methodology was based on the procedures reported by:

Smolka, A J, Goldenring, J R, Gupta, S and Charles E Hammond, CE. Inhibition of gastric H,K-ATPase activity and gastric epithelial cell IL-8 secretion by the pyrrolizine derivative ML 3000. (2004). *BMC Gastroenterology*. 4: 4.

Chailler, P and Menard, D (2005). Establishment of Human Gastric Epithelial (HGE) Cell Lines Exhibiting Barrier Function, Progenitor, and Prezymogenic Characteristics. *Journal of Cellular Physiology* 202: 263-274.

Trainer, D. L., Kline, T., McCabe, F. L., Faucette, L. F., Field, J., Chaikin, M., Anzano, M., Rieman, D., Hoffstein, S., Li, D-J., Gennaro, D., Buscarino, C., Lynch, M., Poste, G. And Greig, R. (1988). Biological characterization and oncogene expression in human colorectal carcinoma cells lines. *International Journal of Cancer* 41: 287-296.

Sample Preparation

The test items were dissolved in 15% ethanol (ETOH)/ Hanks Balanced Salt Solution (HBSS) at concentrations given in the following table.

TABLE 4

Concentrations of the test samples used in this project
Sample Preparation

| No | Sample | Stock Concentrations | Working Solution in 15% ETOH/HBSS | Final Conc. in Well |
| --- | --- | --- | --- | --- |
| #2 | CD1 Cyclodextrin Propolis Complex | powder | 2 mg/ml solids | 200 µg/ml solids |
| #3 | CD2 Cyclodextrin + CAPE | powder | 2 mg/ml solids | 200 µg/ml solids |
| #4 | 25% Propolis Tincture | 250 mg/ml solids | 2 mg/ml solids | 200 µg/ml solids |
| #5 | CAVAMAX W8 Food gamma Cyclodextrin | powder | 2 mg/ml solids | 200 µg/ml solids |

Sample #4 was diluted 50-fold to give a working stock solution of 2 mg/mL solids.
Samples #2, #3 and #5 were powders. Working stock solutions were prepared by weighing 2 mg and dissolving in 1 ml of 15% ETOH/HBSS.

Experimental Procedures

Characterisation of the Test System

1. Human colorectal adenocarcinoma cells (ATCC CCI-221, DLD-1).
2. Penicillin-streptomycin solution: 10000 units/ml penicillin, 10 mg/ml streptomycin in 0.9% NaCl (Sigma Cat #P-0781). Stored at −20° C.
3. DMEM culture medium (Invitrogen Cat #12100-046) Stored at −20° C.
4. Trypsin-EDTA solution: 0.25% Trypsin/EDTA, Invitrogen Cat#15400054 (×10 in stock).
5. Phosphate buffered saline (PBS) (Prepared by TBL).
6. Hanks Balanced Salt Solution (HBSS). (GIBCO Cat No. 14185-052). Stored at 4° C.
7. Foetal Bovine Serum (GIBCO Cat #10091-148). Stored at −20° C.
8. MTT Reagent: 100 mg/vial, (SIGMA Cat. No. M-2128) dissolved in PBS at 10 mg/ml and stored at −20° C. 5 mg/ml MTT solution were prepared in PBS and stored at 4° C. as working solution.
9. MTT lysis buffer: 10% sodium dodecyl sulphate (SDS)/ 45% Dimethyl Formamide (20 g SDS was dissolved in 100 ml of double-distilled water (DDW), and 90 ml of Dimethyl Formamide added to the SDS solution). The pH was adjusted to 4.7 by glacial acetic acid, and DDW added up to a final volume of 200 ml.
10. 5-Fluorouracil (5-FU), (Sigma Cat. No. F-6627). Two working solutions were prepared at 150 ng/ml and 75 ng/ml, dissolved in 15% Ethanol/HBSS. Final concentrations were 7.50 ng/ml and 3.75 ng/ml.

Medium Preparation

The medium for the propagation of the colorectal adenocarcinoma (DLD-1) cells was DMEM, supplemented with penicillin-streptomycin solution (10 ml per liter). FBS was added just before use to give 10% w/v.

Culturing of Cells

1. The human colorectal adenocarcinoma cells (DLD-1) obtained from the American Type Culture Collection USA were revived from cryostorage.
2. Following initial propagation using the media described above (see Medium Preparation), the culture was subcultured using the trypsin-EDTA as follows. The media was removed and 5 ml of the trypsin-EDTA solution added and incubated at 37° C. for 5 min or until all the cells had detached. The trypsin was neutralised by adding an equal volume of DMEM medium and the culture centrifuged at 300 g (1200 rpm) for 5 min at 4° C.

3. The supernatant was decanted and the cell pellets resuspended in medium DMEM, FBS (10%), penicillin (100 units/ml), streptomycin (100 µg/ml). The cells were cultured at 37° C. in 5% $CO_2$/95% air.
4. After reaching confluence, the cells were detached using trypsin-EDTA and centrifuged as described in 2 above.
5. The supernatants were discarded and the cells resuspended in DMEM and supplements as described in 3 above at $7.5 \times 10^4$ cells per ml. A total volume of 23 mls of the cell suspension was required.
6. Into each well of three 96 well plates, 180 µl of the cells (13,550 cells/well) or medium was added as indicated in the plate layout below. The plates were incubated at 5% $CO_2$/95% air at 37° C. for 8 h which was sufficient to allow the cells to strongly adhere.
7. To each well, 20 µl of each of the test samples or positive control was added as indicated in the diagrams above. To the wells labelled 'medium' or 'cells only', 20 µl of 15% ETOH/HBSS was added. Each sample was assessed in replicates of 6, while the controls on all three plates were assessed in replicates of 9 (combined triplicates)
8. The total volume in each well was 200 µl.
9. The plates were incubated at 37° C. in 5% $CO_2$/95% air for 19 h.

Cell Proliferation Assay
1. On completion of the incubation, 20 µl of MTT working solution (5 mg/ml) was added to all wells and incubated for 2 hr at 37° C. in 5% $CO_2$/95% air.
2. 100 µl of MTT lysis buffer was then added and the plates incubated for 3 hr at 37° C. on a shaker in 5% $CO_2$/95% air, followed by pipetting to break up and dissolve the crystals until fully solubilized. The plates were centrifuged at 1200 rpm for 10 minutes to pelletize any remaining insoluble material. From each well 200 µl aliquots were transferred to fresh 96 well plates. The plates were read by a VersaMax microplate reader at 570 nm.
3. Results were expressed as the percentage proliferation of cells cultured in the presence of the sample in comparison to the cells only control. The blank reading was subtracted from all wells as a background reading.

Results and Discussion

Figure 1B:
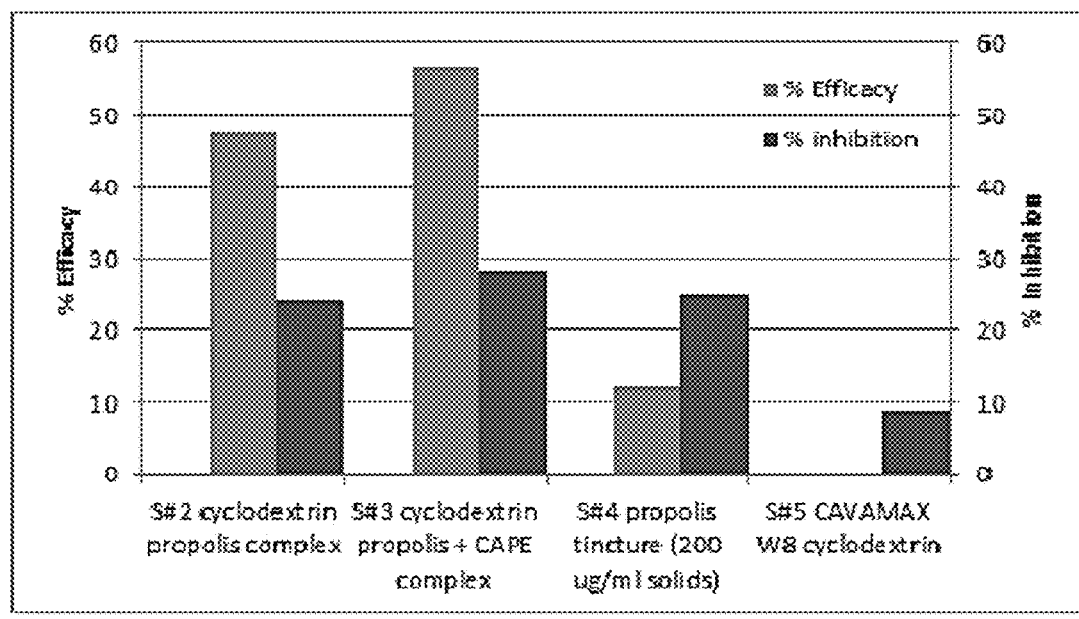

A summary of the effects of controls and test samples on the proliferation of the cells is presented in Table 5 and in FIGS. 1A and 1B.

TABLE 5

Effects of the test samples on the proliferation of the DLD-1 cells. Viability of Human Colon Cancer Cells (DLD-1) as Measured by the MTT Assay.

| Sample ID | Mean (OD 570 nm) | SEM | p Values (<0.05) | % Inhibition |
|---|---|---|---|---|
| Cells only (n = 9) | 0.7047 | 0.0252 | 1.00000000 | 0.00 |
| Cells + 5-FU (7.50 ng/ml). (n = 9) | 0.6575 | 0.0172 | NS | 6.69 |
| Cells + S#2 CD1 Cyclodextrin Propolis Complex (200 µg/ml). (n = 6) | 0.5363 | 0.0161 | 0.00024874 | 23.90 |
| Cells + S#3 CD2 Cyclodextrin & CAPE (200 µg/ml). (n = 6) | 0.5057 | 0.0155 | 0.00004986 | 28.24 |
| Cells + S#4 25% Propolis Tincture (200 µg/ml). (n = 6) | 0.5295 | 0.0339 | 0.00097212 | 24.86 |
| Cells + S#5 CAVAMAX W8 Food gamma Cyclodextrin (200 µg/ml). (n = 6) | 0.6405 | 0.0365 | NS | 9.11 |

TABLE 5-continued

Effects of the test samples on the proliferation of the DLD-1 cells. Viability of Human Colon Cancer Cells (DLD-1) as Measured by the MTT Assay.

| Sample ID | Mean (OD 570 nm) | SEM | p Values (<0.05) | % Inhibition |
|---|---|---|---|---|

NS = Not Significant.

The relatively rapid proliferation rate of the cells observed during the growth of the stock cell culture allowed the incubation time of the cells with the test samples to be reduced to 8 hours. This proved to be quite satisfactory as assessed by the colour intensity of the control culture following reaction with MTT (Mean $OD_{570\ nm}$=0.7047). Each sample was assayed in replicates of six. There was good consistency within the six samples, such that the SEM. for all replicates was within expected limits and all six were used in the calculation of the mean absorbance values. For the controls (both negative and positive) nine replicates were sufficiently consistent to be used for the statistical evaluations.

CD1 Cyclodextrin Propolis Complex

Cyclodextrin Propolis Complex at 200 µg/ml was a statistically significant inhibitor of the proliferation of the colon cancer cells. It reduced proliferation by 23.9%.

CD2 Cyclodextrin Propolis+CAPE

The preparation Cyclodextrin propolis+CAPE at 200 µg/ml was also statistically significant as an inhibitor of the cell growth. It reduced proliferation by 28.2%.

25% Propolis Tincture

The 200 µg/ml concentration of 25% Propolis Tincture was a statistically significant inhibitor of colon cancer growth. It reduced proliferation by 24.9%

CA VAMAX W8 Food Gamma-Cyclodextrin

At 200 µg/ml CAVAMAX W8 Food gamma-cyclodextrin caused an insignificant effect on the proliferation of the cells with a reduction of only 9.1%.

In this study the 5-Fluorouacil at 7.5 ng/ml produced an insignificant 6.7% inhibition of the growth. This was unexpected. Based on previous studies it was anticipated that, at this concentration, a statistically significant reduction would be recorded.

The assays described above were performed on an equivalent mass basis of the test material. Thus, for the native propolis tincture, where the final concentration of test material was 200 µg/mL, the entire 200 µg comprised propolis solids. The cyclodextrin complexes contained at most 25% propolis, and so only 50 of the 200 µg comprised propolis. As can clearly be seen in FIGS. 1A and 1B and as observed above, approximately the same activity for native propolis (ex-tincture) and the propolis/gamma-cyclodextrin composition was observed. Accordingly, this data suggests that this example of a propolis/gamma-cyclodextrin composition of the invention exhibits approximately four times the activity in this assay compared to native propolis, since the content of propolis solids in the complex is only 50 µg/mL (See FIG. 1B).

Table 6 below and FIG. 1B show the % Efficacy for each propolis-containing sample, wherein % Efficacy=% Inhibition/concentration of propolis in the sample.

TABLE 6

Efficacy of test samples

| Sample | % inhibition | [effective propolis] | Efficacy |
|---|---|---|---|
| Propolis/CD complex | 23.9 | 50 | 47.8 |
| Propolis/CD + CAPE complex | 28.2 | 50 | 56.4 |
| Propolis tincture | 24.9 | 200 | 12.45 |
| CD | 9.1 | 0 | — |

The applicants also note that doubling the amount of CAPE present in the cyclodextrin complex only marginally increases the bioactivity, which suggests that CAPE at this concentration is not having a large effect on proliferation.

These data support the enhanced efficacy of compositions of the invention compared to propolis. Without wishing to be bound by any theory, the applicants suggest this may be due to an unexpected synergistic effect on colorectal cell proliferation exhibited by the propolis and cyclodextrin composition.

Example 3

This example shows the effectiveness of the cyclodextrin-encapsulated propolis compared to pure standards of CAPE, chrysin and galangin. All samples were tested against the same human colorectal adenocarcinoma cell line DLD-1 used in Example 2.

Materials and Methods

The test method and experimental procedure are the same as those used in Example 2. CAPE, galangin and chrysin standards were obtained at greater than 99% purity from Sigma-Aldrich. The CAPE, chrysin and galangin concentrations are given in Table 7.

TABLE 7

Test concentrations of CAPE, chrysin and galangin
Samples tested

| No | Sample | CAPE | Chrysin | Galangin |
|---|---|---|---|---|
| S#2 | Cyclodextrin propolis Complex | 0.41 µg/ml solids | 1.07 µg/ml solids | 1.61 µg/ml solids |
| S#3 | Cyclodextrin propolis + CAPE | 0.98 µg/ml solids | 1.06 µg/ml solids | 1.58 µg/ml solids |
| S#4 | 25% Propolis Tincture, 200 µg/ml solids | 1.48 µg/ml solids | 3.91 µg/ml solids | 5.87 µg/ml solids |
| S#6 | CAPE | 200 µg/ml solids | | |
| S#7 | Chrysin | | 200 µg/ml solids | |
| S#8 | Galangin | | | 200 µg/ml solids |

The following samples were tested at a well concentration of 200 µg/ml except as specified in Table 8.

Results and Discussion

TABLE 8

Effects of cyclodextrin complexes and pure compounds on the proliferation of DLD-1 cells
Viability of Human Colon Cancer Cells
(DLD-1) as Measured by the MTT Assay.

| Sample ID | Mean (OD 570 nm) | SEM | p Values (<0.05) | % Inhibition |
|---|---|---|---|---|
| Cells only (n = 9) | 0.3239 | 0.0135 | NS | 0.00 |
| Cells + 5-FU (0.65 µg/ml). (n = 9) | 0.3023 | 0.0154 | NS | 6.66 |
| Cells + 5-FU (1.95 µg/ml). (n = 9) | 0.2689 | 0.0116 | .00534 | 16.96 |
| Cells + S#2 CD1 Cyclodextrin Propolis Complex (200 µg/ml). (n = 6) | 0.5363 | 0.0161 | 0.00024874 | 23.90 |
| Cells + S#3 CD2 Cyclodextrin & CAPE (200 µg/ml). (n = 6) | 0.5057 | 0.0155 | 0.00004986 | 28.24 |
| Cells + S#4 25% Propolis Tincture (200 µg/ml). (n = 6) | 0.5295 | 0.0339 | 0.00097212 | 24.86 |
| S#6 CAPE (200 µg/ml). (n = 5) | 0.0777 | 0.0071 | 7.43E−8 | 76.01 |
| S#7 Chrysin (200 µg/ml). (n = 6) | 0.1233 | 0.0099 | 3.71E−8 | 61.92 |
| S#8 Galangin (200 µg/ml). (n = 6) | 0.1411 | 0.0038 | 6.74E−8 | 56.45 |

Figure 2:
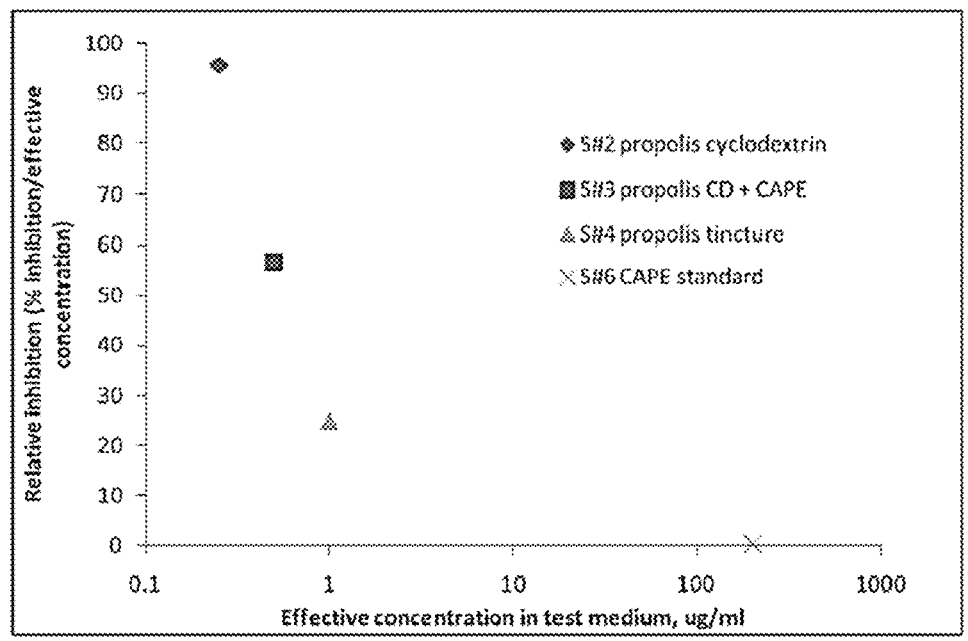
FIG. 2. A comparison of the efficacy of CAPE in compositions of the invention versus pure CAPE. Efficacy is presented as the relative inhibition (% inhibition/effective concentration in the test medium) versus effective concentration. A high value equates to a high efficacy.

As shown in Table 8, the CAPE, chrysin and galangin standards were all statistically significant inhibitors of DLD-1 proliferation at a concentration of 200 µg/ml. The proliferation is also significant when these compounds are present at much lower concentrations in the cyclodextrin complexes. The relative inhibition (ratio of % inhibition to concentration) versus the test substance concentration is shown in FIG. 2.

The results show that encapsulation of propolis containing these three compounds in cyclodextrin greatly increases their activity.

Example 4

This example demonstrates the ability of compositions of the invention, cyclodextrin encapsulated propolis to induce apoptosis in the human colorectal cancer cell line HCT-116, and to augment the apoptotic effect of butyrate in this human colorectal cancer cells, and a cancer cell line HCT-116 R made resistant to butyrate. Butyric acid is generated by intestinal microflora resulting from the digestion of soluble fibre.

Materials and Methods

Cell Culture and Chemicals

The human colorectal cell line HCT-116 was obtained from the American Type Culture Collection (Rockville, Md.). The butyrate resistant cell line was derived from HCT-116 by culturing the parental cells in increasing concentrations of butyrate as previously described in Bordonaro M, Lazarova D L, Sartorelli A C. The activation of beta-catenin by Wnt signaling mediates the effects of histone deacetylase inhibitors. *Exp Cell Res.* 2007; 313:1652-66 (including references therein).

Colorectal cells were grown in alpha-MEM medium with 10% fetal bovine serum and antibiotics. The concentration of CAPE in the propolis-cyclodextrin complex CD1 was 1.79 µg/100 µg propolis solid encapsulated in the cyclodextrin, or 0.41 µg/100 µg cyclodextrin complex. Stock solutions were prepared in dimethyl sulfoxide, except for butyrate, which was dissolved in water at 1 M concentration.

Apoptotic Assays

Twenty-four hours prior to treatments, colon cancer cells were plated in 24-well plates at 100,000-120,000 per well. A negative control of cells only was compared to cells exposed to a positive control of 5 mM butyrate; 1.2 ug/ml CAPE; 5 mM butyrate+1.2 ug/ml CAPE, 100 ug/ml propolis-cyclodextrin, or 5 mM butyrate+100 ug/ml propolis-cyclodextrin for 50 hours. All cells (floating and attached) were harvested and stained for apoptotic and necrotic markers using a PE Annexin V Apoptosis Detection Kit I (BD Biosciences, #559763). Flow cytometry analyses were carried out with FACS Aria II and DiVa software. Percent apoptosis is the number or apoptotic cells divided by the number of all analyzed cells, and multiplied by 100.

Statistics

All data are presented as mean±standard deviation from at least three sets of independent experiments. Student T-test analysis was used to determine the significance of statistical differences. Differences were considered significant at $P<0.05$.

Results

The Apoptotic Effect of Butyrate on Colon Cancer Cells is Augmented to Different Extent by CAPE and Propolis.

Figure 3:
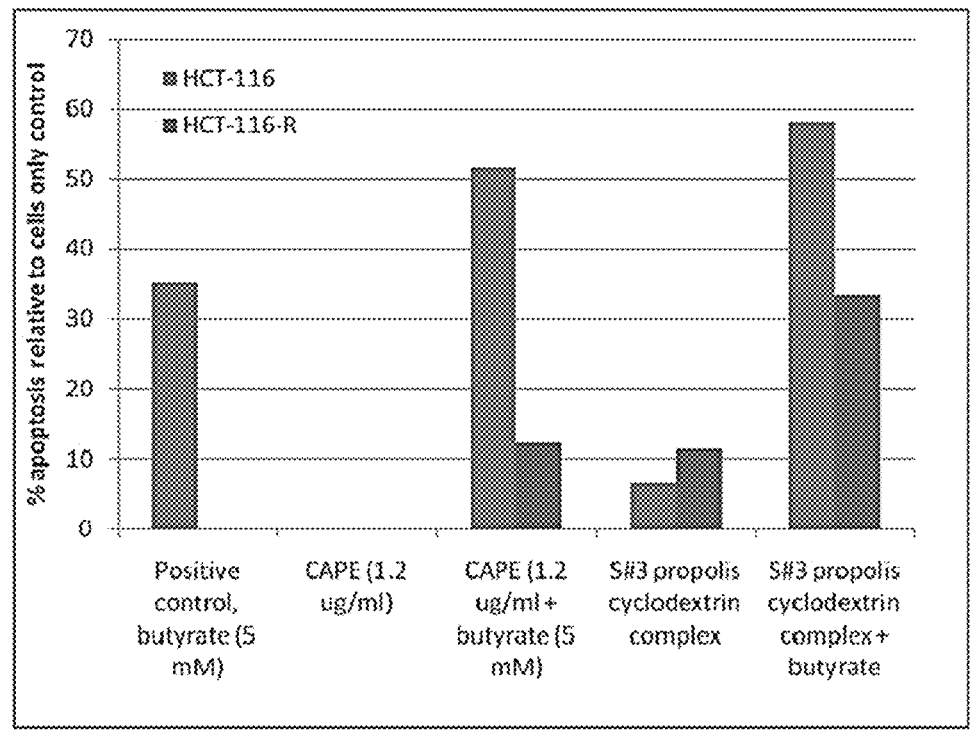
FIG. 3. Effect of CAPE, European propolis cyclodextrin complex, butyrate and mixtures thereof on apoptosis of HCT-116 and HCT-116-R cells relative to a negative control (cells only).

HCT-116 and HCT-R cells were utilized to compare the apoptotic effect of butyrate, CAPE and propolis-cyclodextrin complex, and combinations of butyrate and CAPE or propolis cyclodextrin. The results are shown in Table 9 and in FIG. 3 after normalization against the negative control.

TABLE 9

Effect of pure compounds, propolis gamma cyclodextrin complex CD1 and their mixtures with butyrate on the apoptosis of HCT-116 and HCT-116 R cells

| Sample I.D. | HCT-116 % Apoptosis | Error | HCT-116-R % Apoptosis | Error |
| --- | --- | --- | --- | --- |
| Negative control, cells only | 22.3 | ±4.4 | 12.1 | ±1.0 |
| Positive control, butyrate (5 mM) | 57.5 | ±1.5 | 11.2 | ±2.1 |
| CAPE (1.2 ug/ml) | 18.3 | ±5.8 | 9.7 | ±1.2 |
| CAPE (1.2 ug/ml + butyrate (5 mM) | 74 | ±4.3 | 24.3 | ±4.3 |
| S#3 propolis cyclodextrin complex | 28.7 | ±4.9 | 23.4 | ±4.9 |
| S#3 propolis cyclodextrin complex + butyrate | 80.5 | ±1.4 | 45.5 | ±1.4 |

HCT-116 cells exposed to CAPE had no significant increase in apoptosis relative to the negative control. HCT-116 cells exposed to the propolis-cyclodextrin complex CD1 underwent significant levels of apoptosis at around 8% higher than the negative control (see FIG. 3), despite the propolis-cyclodextrin complex having only approximately ¼ of the CAPE. Butyrate treatment of HCT-116 cells resulted in 35% apoptosis relative to cells only. The combination of CAPE or propolis-cyclodextrin and butyrate augmented the apoptosis of HCT-116 cells achieved with butyrate. The combination of CAPE and butyrate resulted in 52% apoptosis relative to cells only ($P<0.05$ compared to butyrate alone). The combination of propolis-cyclodextrin and butyrate resulted in 58% apoptosis relative to cells only ($P<0.05$ compared to butyrate alone), despite having only ¼ of the CAPE. HCT-R cells did not undergo significant apoptosis when tested with butyrate alone (as expected) or CAPE alone; however, exposure to the propolis-cyclodextrin complex resulted in significantly higher levels of apoptosis relative to the negative control of 11%, $P<0.05$. The combination of CAPE or propolis-cyclodextrin and butyrate re-sensitized HCT-R cells to the apoptotic effect of butyrate. The combination of CAPE and butyrate resulted in 12% apoptosis relative to the control ($P<0.05$ compared to butyrate alone). The combination of propolis-cyclodextrin complex and butyrate further enhanced apoptosis to 33% relative to the control, ($P<0.05$ compared to butyrate alone).

Discussion

This example shows that caffeic acid phenethyl ester (CAPE), and a propolis-cyclodextrin complex containing a ¼ of the amount of CAPE tested alone, exert differential effects on apoptosis in human colon cancer cells. The propolis-cyclodextrin composition augmented apoptosis of colon cancer cells exposed to butyrate to a much greater extent than CAPE, which is ineffective by itself at the concentration used. Furthermore, the propolis-cyclodextrin complex was more potent than CAPE in resensitizing butyrate-resistant HCT-R cells to butyrate-induced apoptosis.

It is expected that a diet containing soluble fibre digestible by intestinal microflora will generate butyrate in-situ, and that colon cancer cells could become resistant to butyrate generated in such a manner, or administered by other means due to prolonged exposure. This example demonstrates the efficacy of compositions of the invention for modulating the apoptosis of both native and butyrate resistant colorectal cancer cells, both without and with a second apoptotic agent; and that the compositions of the invention can reverse the resistance of colorectal cells to apoptosis induced by such agents. These results support the efficacy of compositions of the invention in the treatment and prevention of gastrointestinal cancers.

Example 5

This example demonstrates the ability of compositions of the invention, γ-cyclodextrin encapsulated European-type propolis to inhibit proliferation of the human colon cancer adenocarcinoma cell line, DLD-1; human colon cancer cell line, HCT-116; human gastric carcinoma cell line, NCI-N87; and human oesophageal squamous cell carcinoma cell line, KYSE-30. The general method used for Examples 5-8 is shown below.

Materials and Methods for the Gastro-Intestinal Cancer Anti-Proliferative Assays Sample CD5 γ-cyclodextrin as prepared in Example 1 was assessed for its ability to modulate the viability and proliferation of human colorectal adenocarcinoma cells (DLD-1); human colon cancer cell line (HCT-116); human gastric carcinoma cell line (NCI-N87); and human oesophageal squamous cell carcinoma cell line (KYSE-30) as assessed by the MTT assay. The positive control, 5-fluorouracil (5-FU) was included at three concentrations; in addition to an unsupplemented cell control as a negative control in the study. [Do we include test compounds for comparison?.

Description of Test Materials and Test Methods

The four human gastrointestinal carcinoma cell lines were revived from cryostorage and cultured in the presence of the test and reference samples. An MTT assay was then performed on the cultures to determine the effect of the samples on the cell viability and proliferation.

The methodology is based on the procedures outlined in Example 2 above.

Sample Preparation

The test sample, and all other test samples in Examples 5-8 were dissolved in 15% ethanol/Hanks Balanced Salt Solution (ETOH)/HBSS to a concentration of 2 mg/mL solids. In the assay the final concentration of the samples was 200 μg/ml with a final EtOH concentration of 1.5%.

Experimental Procedures
Characterisation of the Test System
1. Human colorectal adenocarcinoma cells (ATCC CCI-221, DLD-1) (ATCC, Bethesda, Md., USA)
2. Human gastric carcinoma cells (ATCC CRL-5822, NCI-N87) (ATCC, Bethesda, Md., USA)
3. Human oesophageal squamous cell carcinoma (ECACC, KYSE-30) (Sigma Aldrich, Auckland, NZ)
4. Human colon carcinoma cells (ECACC HCT-116) (Sigma Aldrich, Auckland, NZ)
5. Penicillin-streptomycin solution: 10000 units/ml penicillin, 10 mg/ml streptomycin in 0.9% NaCl (Sigma Cat #P-0781). Stored at −20° C.
6. For DLD-1 cells: DMEM culture medium (Invitrogen Cat #12100-046). Stored at 40° C.
7. For NCI-N87 cells: RPMI-1640 medium modified to contain 2 mM L-glutamine, 10 mM HEPES, 1 mM sodium pyruvate, 4500 mg/L glucose, and 1500 mg/L sodium bicarbonate (Sigma R6504). Stored at 4° C.
8. For KYSE-410 cells: RPMI-1640 medium modified to contain 2 mM L-glutamine (Sigma R6504). Stored at 4° C.
9. For HCT-116 cells: McCoy's 5 A medium modified to contain 2 mM L-glutamine (Sigma M48792). Stored at 4° C.
10. Trypsin-EDTA solution: 0.25% Trypsin/EDTA, Invitrogen Cat#15400054 (×10 in stock).
11. Phosphate buffered saline (PBS) (Prepared by TBL).
12. Hanks Balanced Salt Solution (HBSS). (GIBCO Cat No. 14185-052). Stored at 4° C.
13. Foetal Bovine Serum (GIBCO Cat #10091-148). Stored at −20° C.
14. MTT Reagent: 100 mg/vial, (SIGMA Cat. No. M-2128) dissolved in PBS at 10 mg/ml and stored at −20° C. 5 mg/ml MTT solution will be prepared in PBS and stored at 4° C. as working solution.
15. MTT lysis buffer: 10% sodium dodecyl sulphate (SDS)/45% Dimethyl Formamide (20 g SDS will be dissolved in 100 ml of double-distilled water (DDW), and 90 ml of Dimethyl Formamide will be added to the SDS solution). The pH will be adjusted to 4.7 by glacial acetic acid, and DDW added up to a final volume of 200 ml.
16. 5-Fluorouracil (5-FU), (Sigma Cat. No. F-6627). Three working solutions will be prepared at 19.5 µg/ml. 6.5 µg/ml and 1.95 µg/ml dissolved in 15% Ethanol/HBSS. Final concentrations will be 1.95 µg/ml (15 µM), 0.65 µg/ml (5 µM) and 0.195 µg/ml (1.5 µM).

Medium Preparation

The medium for the propagation of the each of the cells lines is given above. Each medium was prepared following the ATCC/ECACC instructions and supplemented with penicillin-streptomycin solution (10 ml per liter). FBS (at 10%) was added just before use.

Culturing of Cells
1. Each of the cell lines obtained from either the American Type Culture Collection USA, or the European Collection of Cell Cultures was revived from cryostorage.
2. Following initial propagation using the media described above (see Characterisation of Test System, and Medium Preparation), the culture was subcultured using trypsin-EDTA. The media was removed and 5 ml of the trypsin-EDTA solution added and incubated at 37° C. for 5 min or until all the cells have detached. The trypsin was neutralised by adding an equal volume of the relevant medium and centrifuging the suspension at 300 g (1200 rpm) for 5 min at 4° C.
3. The supernatant was decanted and the cell pellets resuspended in the relevant medium containing FBS (10%), penicillin (100 units/ml), streptomycin (100 µg/ml).
4. After reaching confluence, the cells were detached using trypsin-EDTA as described in 2 above and centrifuged.
5. The supernatants were discarded and the cells resuspended in the relevant medium and supplements as described in 3 above at $1.0 \times 10^4$ cells per ml. A total volume of approximately 54 mls of each cell suspension was required.
6. Into each well of six 96 well plates, 180 µl of the cells (1,800 cells/well) or medium was added as indicated in predetermined plate layouts. The plates were incubated at 5% $CO_2$/95% air at 37° C. for ~48 hrs to allow the cells to adhere.
7. To each well, 20 µl of each of the test compounds or 5-FU was added as indicated in the plate layouts. For negative control wells labelled 'medium' or 'cells only', 20 µl of 15% ETOH/HBSS was added. Each sample or control was assessed in replicates of 3 or 6.
8. The total volume in each well was 200 µl.
9. The plates were incubated at 37° C. in 5% $CO_2$/95% air for 24 hr.

Cell Proliferation Assay
1. On completion of the incubation, 20 µl of MTT working solution (5 mg/ml) was added to all wells and incubated for 3-4 hr at 37° C. in 5% $CO_2$/95% air. The plates were monitored every 30-60 minutes and if a few cells showed the presence of crystals then the lysis buffer was added as in Step 2 below.
2. 100 µl of MTT lysis buffer was then added and the plates incubated overnight at 37° C. in 5% $CO_2$/95% air. The plates were centrifuged at 1200 rpm for 10 minutes to pellet any remaining insoluble material. From each well 200 µl was transferred to fresh 96 well plates. The plates were then read in a VersaMax microplate reader at 550 nm.
3. The blank reading was subtracted from all wells as a background reading. Results were expressed as the percentage proliferation of cells cultured in the presence of the sample in comparison to the cells only control.
4. A VersaMax 96-well plate reader was used to colorimetrically (at 550 nm) assess the proliferation of the cells.
5. The percentage standard error of the mean was assessed and extreme outliers will be removed if the SEM %>15. Preliminary statistical significance will be assessed with an independent Student t-test at $\alpha \leq 0.05$ (with and without outliers).

Observations Regarding the Test Method

The culturing of the several cancer cells in the presence of the various test preparations and the 5-FU was conducted for 48 hours as the visual observation of the cell density of the negative controls of the DLD-1 and NCI-N87 after 24 hours suggested that the growth was not as rapid as anticipated. For consistency the time for the other cultures was set as the same.

The study plan required outliers among the replicates to be deleted from the calculations if the percentage standard error of mean (SEM) was greater than 15%. When a sample is a strong antagonist, the absorbance values are small. Consequently small changes among these mean that the variance from the mean expressed as a percentage is relatively large when compared with less inhibitory samples. This has resulted in some outliers in which virtually complete inhibition occurred being removed from the analysis.

Results

The results of the cell proliferation assay for CD5 γ-cyclodextrin are shown in Table 10, along with results for the positive control 5-fluorouracil (5-FU) at three concentrations, and the negative control (cells only with medium and no test compound or positive control). In the Table, OD is Optical Density measured at 570 nm; SEM is the Standard Error associated with the Mean Optical Density value measured; p is the probability value that the measurement is statistically significant via the Student t-test, here taken to be <0.05; % stim. is the percentage stimulation of proliferation compared to the negative control (test compound inactive); % inhibition is the percentage reduction of proliferation compared to the negative control, with a large number indicating the test compound has anticancer proliferation potential.

TABLE 10

Antiproliferative activity of CD5 γ-cyclodextrin encapsulated European-type propolis against 4 gastro-intestinal cell lines

| Cell type | Sample | Mean OD (570 nm) | SEM | p values (<0.05) | % stim. | % inhibition |
|---|---|---|---|---|---|---|
| DLD-1 | Cells only (n = 6) | 0.4122 | 0.0104 | 1 | 0 | 0 |
| | Cells + 5FU (0.195 µg/ml, n = 6) | 0.3029 | 0.0074 | 6.36E−06 | 0 | 26.53 |
| | Cells + 5FU (0.65 µg/ml, n = 6) | 0.2584 | 0.0113 | 1.59E−06 | 0 | 37.31 |
| | Cells + 5FU (1.95 µg/ml, n = 6) | 0.2409 | 0.0073 | 9.50E−08 | 0 | 41.56 |
| | Cells + CD5 | 0.1114 | 0.0029 | 8.00E−11 | 0 | 73 |
| HCT-116 | Cells only (n = 6) | 0.5084 | 0.0321 | 1.00E+00 | 0 | 0 |
| | Cells + 5FU (0.195 µg/ml, n = 6) | 0.336 | 0.019 | 9.50E−04 | 0 | 33.92 |
| | Cells + 5FU (0.65 µg/ml, n = 6) | 0.234 | 0.015 | 1.50E−05 | 0 | 53.97 |
| | Cells + 5FU (1.95 µg/ml, n = 6) | 0.2169 | 0.0037 | 4.10E−06 | 0 | 57.34 |
| | Cells + CD5 | 0.1051 | 0.0071 | 2.40E−07 | 0 | 79.33 |
| NCI-N87 | Cells only (n = 6) | 0.4417 | 0.025 | 1 | 0 | 0 |
| | Cells + 5FU (0.195 µg/ml, n = 6) | 0.4085 | 0.0081 | >0.05 | 0 | 7.52 |
| | Cells + 5FU (0.65 µg/ml, n = 6) | 0.3656 | 0.0212 | 0.043 | 0 | 17.22 |
| | Cells + 5FU (1.95 µg/ml, n = 6) | 0.3702 | 0.0055 | 0.019 | 0 | 16.19 |
| | Cells + CD5 | 0.2973 | 0.0069 | 2.40E−04 | 0 | 32.68 |
| KYSE-30 | Cells only (n = 6) | 0.6017 | 0.0223 | 1 | 0 | 0 |
| | Cells + 5FU (0.195 µg/ml, n = 6) | 0.4588 | 0.0107 | 1.80E−04 | 0 | 23.75 |
| | Cells + 5FU (0.65 µg/ml, n = 6) | 0.3647 | 0.0188 | 1.00E−05 | 0 | 39.38 |
| | Cells + 5FU (1.95 µg/ml, n = 6) | 0.316 | 0.0045 | 1.90E−07 | 0 | 47.48 |
| | Cells + CD5 | 0.1773 | 0.0069 | 5.30E−09 | 0 | 70.54 |

Discussion

CD5 γ-cyclodextrin was highly active against three of the four cell lines resulting in inhibition of proliferation of human colon adenocarcinoma cell line DLD-1 by 73.0%, human colon cancer cell line HCT-116 by 79.3%, human gastric carcinoma cell line NCI-N87 by 32.7% and human oesophageal squamous cell carcinoma cell line KYSE-30 by 70.5%.

The degree of inhibition was similar to that achieved using the known anticancer agent 5-fluororacil (5-FU), and indeed superior for NCI-N87. The results demonstrate that the γ-cyclodextrin encapsulated European-type propolis has broad spectrum anti-proliferative activity for gastrointestinal cancers. The results also confirm the anti-cancer activity against human colon adenocarcinoma cell line DLD-1 demonstrated in Examples 2-4, and anti-cancer activity against human colon cancer cell line HCT-116 demonstrated in Example 4.

Example 6

This example demonstrates the ability of compositions of the invention, α-cyclodextrin encapsulated European-type propolis to inhibit proliferation of the human colon cancer adenocarcinoma cell line, DLD-1; human colon cancer cell line, HCT-116; human gastric carcinoma cell line, NCI-N87; and human oesophageal squamous cell carcinoma cell line, KYSE-30. This study was performed using proliferation assays for DLD-1; HCT-116; NCI-N87; KYSE-30.

The α-cyclodextrin encapsulated European-type propolis used in the assays at a concentration of 200 µg/ml was manufactured as per Example 1, test substance CD6 with composition given in Table 2. The same test procedure given in detail in Example 5 was also used for Example 6.

Results

The results of the antiproliferation assays for α-cyclodextrin encapsulated European-type propolis are shown in Table 11. The results for the cells only (negative control), and for the 5-FU positive controls are the same as for Example 5 and so are not included in the table.

TABLE 11

Antiproliferative activity of CD6 α-cyclodextrin encapsulated European-type propolis against 4 gastro-intestinal cell lines

| Cell type | Mean OD (570 nm) | SEM | P values (<0.05) | % stim. | % inhibition |
|---|---|---|---|---|---|
| DLD-1 | 0.158 | 0.0069 | 1.80E−09 | 0 | 61.67 |
| HCT-116 | 0.2147 | 0.0157 | 9.30E−06 | 0 | 57.78 |
| NCI-N87 | 0.3329 | 0.0068 | 1.80E−03 | 0 | 24.62 |
| KYSE-30 | 0.3088 | 0.0071 | 1.90E−07 | 0 | 48.67 |

Discussion

CD6 α-cyclodextrin was moderately active against two of the four cell lines, resulting in inhibition of proliferation of human colon adenocarcinoma cell line DLD-1 by 61.7%, human colon cancer cell line HCT-116 by 57.8%, human gastric carcinoma cell line NCI-N87 by 24.6% and human oesophageal squamous cell carcinoma cell line KYSE-30 by 48.7%.

The degree of inhibition was similar to that achieved using the known anticancer agent 5-fluoracil (5-FU). The results demonstrate that the α-cyclodextrin encapsulated European-type propolis has broad spectrum anti-proliferative activity for gastrointestinal cancers, but the activity is lower than that of γ-cyclodextrin encapsulated European-type propolis.

Example 7

This example demonstrates the ability of compositions of the invention, β-cyclodextrin encapsulated European-type propolis to inhibit proliferation of the human colon cancer adenocarcinoma cell line, DLD-1; human colon cancer cell line, HCT-116; human gastric carcinoma cell line, NCI-N87; and human oesophageal squamous cell carcinoma cell line, KYSE-30. This study was performed using proliferation assays for DLD-1; HCT-116; NCI-N87; and KYSE-30.

The β-cyclodextrin encapsulated European-type propolis used in the assays at a concentration of 200 μg/ml was manufactured as per Example 1, test substance CD7 with composition given in Table 2. The same test procedure given in detail in Example 5 was also used for Example 7.

Results

The results of the antiproliferation assays for α-cyclodextrin encapsulated European-type propolis are shown in Table 12. The results for the cells only (negative control), and for the 5-FU positive controls are the same as for Example 5 and so are not included in the table.

TABLE 12

Antiproliferative activity of CD7 β-cyclodextrin encapsulated European-type propolis against 4 gastro-intestinal cell lines

| Cell type | Mean OD (570 nm) | SEM | P values (<0.05) | % stim. | % inhibition |
|---|---|---|---|---|---|
| DLD-1 | 0.1547 | 0.005 | 7.40E−10 | 0 | 62.48 |
| HCT-116 | 0.2563 | 0.0201 | 5.60E−05 | 0 | 49.6 |
| NCI-N87 | 0.3451 | 0.0062 | 3.70E−03 | 0 | 21.85 |
| KYSE-30 | 0.3438 | 0.003 | 4.40E−07 | 0 | 42.87 |

Discussion

CD7 β-cyclodextrin was moderately active against two of the four cell lines, resulting in inhibition of proliferation of human colon adenocarcinoma cell line DLD-1 by 62.5%, human colon cancer cell line HCT-116 by 49.6%, human gastric carcinoma cell line NCI-N87 by 21.8% and human oesophageal squamous cell carcinoma cell line KYSE-30 by 42.9% The degree of inhibition was similar to that achieved using the known anticancer agent 5-fluoracil (5-FU).

The results demonstrate that the β-cyclodextrin encapsulated European-type propolis has broad spectrum anti-proliferative activity for gastrointestinal cancers, but the activity is lower than that of γ-cyclodextrin encapsulated European-type propolis.

Example 8

This example demonstrates the ability of compositions of the invention, γ-cyclodextrin encapsulated Brazilian-type propolis to inhibit proliferation of the human colon cancer adenocarcinoma cell line, DLD-1; human colon cancer cell line, HCT-116; human gastric carcinoma cell line, NCI-N87; and human oesophageal squamous cell carcinoma cell line, KYSE-30. This study was performed using proliferation assays for DLD-1; HCT-116; NCI-N87; and KYSE-30.

The γ-cyclodextrin encapsulated Brazilian-type propolis used in the assays at a concentration of 200 μg/ml was manufactured as per Example 1, test substance CD8. The same test procedure given in detail in Example 5 was also used for Example 8.

Results

The results of the antiproliferation assays for γ-cyclodextrin encapsulated Brazilian green-type propolis are shown in Table 13. The results for the cells only (negative control), and for the 5-FU positive controls are the same as for Example 5 and so are not included in the table.

TABLE 13

Antiproliferative activity of CD8 γ-cyclodextrin encapsulated Brazilian green-type propolis against 4 gastro-intestinal cell lines

| Cell type | Mean OD (570 nm) | SEM | P values (<0.05) | % stim. | % inhibition |
|---|---|---|---|---|---|
| DLD-1 | 0.3347 | 0.0128 | 8.50E−05 | 0 | 18.82 |
| HCT-116 | 0.3847 | 0.02 | 8.40E−03 | 0 | 24.34 |
| NCI-N87 | 0.4566 | 0.0132 | >0.05 | 3.39 | 0 |
| KYSE-30 | 0.4733 | 0.012 | 4.80E−04 | 0 | 21.35 |

Discussion

CD8 γ-cyclodextrin was moderately to weakly active against three of the four cell lines, resulting in inhibition of proliferation of human colon adenocarcinoma cell line DLD-1 by 18.8%, human colon cancer cell line HCT-116 by 24.3%, and human oesophageal squamous cell carcinoma cell line KYSE-30 by 21.3% The proliferation of human gastric carcinoma cell line NCI-N87 was stimulated by 3.4%, but the stimulation was not significant.

The degree of inhibition was similar to that achieved using the known anticancer agent 5-fluoracil (5-FU) except against NCI-N87, where no effect was seen. The results demonstrate that the γ-cyclodextrin encapsulated Brazilian green-type propolis has relatively broad spectrum anti-proliferative activity for gastrointestinal cancers, but the activity is much lower than that of γ-cyclodextrin encapsulated European-type propolis.

Example 9

This example provides a comparative assessment of the anti-oesophageal cancer activity of European-type NZ cyclodextrin encapsulated propolis CD8 with Brazilian green cyclodextrin-encapsulated propolis CD9; and a comparative assessment of the parent NZ propolis dry solids to Brazilian green propolis solids; and to gamma-cyclodextrin alone. This study was performed using proliferation assays for the human oesophageal squamous cell carcinoma cell line, KYSE-30 using the general method outlined in Example 5. The NZ propolis was the same as used in Example 1 to manufacture complex CD8. The Brazilian green propolis was the same as used in Example 1 to manufacture complex CD9. The NZ propolis contained 5.81 mg/g CAPE, 20.92 mg/g pinobanksin, 43.84 mg/g pinobanksin 3 acetate, 85.17 mg/g pinocembrin, 27.60 mg/g chrysin and 39.74 mg/g galangin. The Brazilian propolis contained 8.36 mg/g artepillin-c, 0.26 mg/g caffeic acid, and 4.31 mg/g para-coumaric acid Results The results of the KYSE-30 cell proliferation assay are shown in Table 14 for the compounds and propolis tincture samples tested, along with results for the positive control 5-fluorouracil (5-FU) at three concentrations, and the negative control (cells only with medium and no test compound or positive control). In the Table, n is the number of replicates; OD is Optical Density measured at 570 nm; SEM is the Standard Error associated with the Mean Optical Density value measured; p is the probability value that the measurement is statistically significant via the Student t-test, here taken to be <0.05 (NS=not significant); % inhibition is the percentage reduction of proliferation compared to the negative control, with a large number indicating the test compound has anticancer proliferation potential.

TABLE 14

Antiproliferative activity of cyclodextrin-encapsulated propolis CD8 and CD9 and propolis dry solids against oesophageal squamous cell carcinoma cell line KYSE-30

| Compound | Concentration | Mean OD (570 nm) | SEM | P values (<0.05) | % inhibition |
|---|---|---|---|---|---|
| Cells only (n = 6) | | 0.3353 | 0.0076 | 1 | 0 |
| 5-FU (n = 6) | 0.195 µg/ml | 0.3238 | 0.0202 | NS | 3.41 |
| 5-FU (n = 6) | 0.65 µg/ml | 0.2795 | 0.0100 | 1.26E−03 | 16.63 |
| 5-FU (n = 6) | 1.95 µg/ml | 0.2297 | 0.0052 | 4.60E−07 | 31.49 |
| NZ propolis dry solids (n = 6) | 200 µg/ml | 0.2358 | 0.0077 | 3.57E−06 | 29.67 |
| Brazilian green propolis (n = 6) | 50 µg/ml | 0.2989 | 0.0131 | 3.72E−02 | 10.86 |
| CD8 Gamma-CD complex NZ propolis (n = 6) | 200 µg/ml | 0.2307 | 0.0079 | 2.55E−06 | 31.18 |
| CD9 Gamma-CD complex Brazilian propolis (n = 6) | 200 µg/ml | 0.3008 | 0.0138 | NS | 10.27 |
| Gamma-CD (n = 6) | 200 µg/ml | 0.3056 | 0.0219 | 2.29E−01 | 8.85 |

Discussion

This example shows that gamma-cyclodextrin encapsulated NZ propolis is more active (31.2% inhibition of proliferation) than the parent NZ propolis dry solids (29.7% inhibition of proliferation), despite only containing approximately ¼ of the propolis dry solids. The activity is similar to the known anticancer agent 5-fluoroacil (5-FU) at the highest test concentration. The results are very similar to that found for the inhibition of proliferation of colon carcinoma cell line DLD-1 in Example 2 by gamma-cyclodextrin encapsulated NZ propolis and NZ propolis dry solids. The gamma cyclodextrin alone inhibited proliferation by 8.8%.

These data support the enhanced efficacy of compositions of the invention compared to propolis for anti-gastrointestinal cancer. Without wishing to be bound by any theory, the applicants suggest this may be due to an unexpected synergistic effect on gastrointestinal cancer cell proliferation exhibited by the NZ propolis and cyclodextrin composition. In contrast, the Brazilian green gamma-cyclodextrin propolis complex has about the same level of activity as the equivalent amount of Brazilian green propolis dry solids, and only slightly higher activity than gamma cyclodextrin by itself against the proliferation of human oesophageal squamous cell carcinoma cell line KYSE-30. These data also show that for this cell line, European-type propolis is the preferred type of propolis for encapsulation by cyclodextrin.

INDUSTRIAL APPLICABILITY

Anti-gastrointestinal cancer compositions of this invention containing propolis or an extract or fraction thereof and cyclodextrin can be used in consumer goods including foods and beverages, medical devices, medical supplies, functional foods and pharmaceuticals. Methods of using such compositions, for example in the treatment of gastrointestinal cancer and symptoms thereof have application in the medical field.

The invention claimed is:

1. A method of treating gastric cancer in a subject, the method comprising administration of an effective amount of a composition comprising propolis and cyclodextrin, to a subject in need thereof, wherein
 (a) the propolis is a propolis extract or fraction,
 (b) the composition comprises a CAPE concentration of from about 1 to about 5 mg/g and a pinocembrin concentration of greater than about 10 mg/g,
 (c) the propolis extract or fraction is entirely encapsulated within the cyclodextrin, and
 (d) the cyclodextrin is gamma-cyclodextrin or chemically modified gamma-cyclodextrin.

2. The method according to claim 1, wherein the composition consists of propolis and cyclodextrin and wherein the propolis is a propolis extract or fraction comprising the CAPE and pinocembrin.

3. The method of claim 1, wherein the composition comprises from about 10% wt to about 70% wt propolis.

4. The method of claim 1 wherein the composition comprises from about 10% wt to about 30% wt propolis.

5. The method of claim 1 wherein the propolis is or comprises propolis resin.

6. The method of claim 5, wherein the composition comprises from about 10% wt to about 70% wt propolis resin or a mixture of propolis resin and propolis or an extract or fraction thereof.

7. The method of claim 6 wherein the composition comprises from about 10% wt to about 30% wt propolis resin or a mixture of propolis resin and propolis or an extract or fraction thereof.

8. The method of claim 1, wherein the molar ratio of propolis to cyclodextrin in the composition is no greater than about 1:1.

9. The method as claimed in claim 1, wherein the propolis has
 (a) a galangin concentration of greater than about 5 mg/g, or
 (b) a chrysin concentration of greater than about 3.5 mg/g, or
 (c) combinations thereof.

10. The method as claimed in claim 1, wherein the composition has
  (a) a galangin concentration of greater than about 1 mg/g, or
  (b) a chrysin concentration of greater than about 1 mg/g, or
  (c) a pinobanksin-3-acetate concentration of from about 9.1 to about 17.5 mg/g, or
  (d) a caffeic acid concentration of greater than about 1 mg/g, or
  (e) any combination of any two or more of (a) to (d) above.

11. The method as claimed in claim 3, wherein the composition comprises from about 10% wt to about 50% wt propolis.

12. The method as claimed in claim 6, wherein the composition comprises from about 10% wt to about 50% wt propolis resin or a mixture of propolis resin and propolis or an extract or fraction thereof.

13. The method as claimed in claim 1 wherein the composition is formulated for oral administration.

14. The method as claimed in claim 1 wherein the composition is formulated for topical administration.

15. The method as claimed in claim 1 wherein the composition is a food, drink, food additive, drink additive, dietary supplement, nutritional product, medical food or nutraceutical.

16. A method of ameliorating the onset or severity of symptoms of gastric cancer in a subject or maintaining symptoms of gastric cancer at a substantially static level in a subject, the method comprising administration of an effective amount of a composition comprising propolis and cyclodextrin, to a subject in need thereof, wherein
  (a) the propolis is a propolis extract or fraction,
  (b) the composition has a CAPE concentration of from about 1 to about 5 mg/g and a pinocembrin concentration of greater than about 10 mg/g,
  (c) the propolis extract or fraction is entirely encapsulated within the cyclodextrin, and
  (d) the cyclodextrin is gamma-cyclodextrin or chemically modified gamma-cyclodextrin.

* * * * *